United States Patent
Kim et al.

(10) Patent No.: US 12,280,148 B2
(45) Date of Patent: Apr. 22, 2025

(54) COMPOSITION FOR PROMOTING EXTRACELLULAR VESICLE PRODUCTION CONTAINING PEPTIDE DERIVED FROM NOXA PROTEIN AND METHOD FOR PRODUCING EXTRACELLULAR VESICLES BY USING SAME

(71) Applicant: Exocalibre Therapeutics Co., Ltd., Gwangju (KR)

(72) Inventors: Tae-Hyoung Kim, Gwangju (KR); Jung Hee Park, Gwangju (KR); Ji Hye Han, Gwangju (KR); Seung-Hyun Myung, Gwangju (KR)

(73) Assignee: Exocalibre Therapeutics Co., Ltd., Gwangju (KR)

( * ) Notice: Subject to any disclaimer, the term of this patent is extended or adjusted under 35 U.S.C. 154(b) by 887 days.

(21) Appl. No.: 17/424,232

(22) PCT Filed: Jun. 3, 2021

(86) PCT No.: PCT/KR2021/006905
§ 371 (c)(1),
(2) Date: Jul. 20, 2021

(87) PCT Pub. No.: WO2022/055077
PCT Pub. Date: Mar. 17, 2022

(65) Prior Publication Data
US 2022/0304931 A1    Sep. 29, 2022

(30) Foreign Application Priority Data

Sep. 9, 2020    (KR) ........................ 10-2020-0115145

(51) Int. Cl.
| | | |
|---|---|---|
| *A61K 38/08* | (2019.01) | |
| *A61K 9/1277* | (2025.01) | |
| *A61K 31/473* | (2006.01) | |
| *A61K 31/704* | (2006.01) | |
| *A61K 35/13* | (2015.01) | |
| *A61K 38/10* | (2006.01) | |
| *A61K 38/17* | (2006.01) | |
| *A61K 38/19* | (2006.01) | |
| *A61K 45/06* | (2006.01) | |
| *A61K 48/00* | (2006.01) | |
| *A61P 35/00* | (2006.01) | |
| *C07K 7/06* | (2006.01) | |
| *C07K 7/08* | (2006.01) | |
| *C07K 14/47* | (2006.01) | |
| *C12N 5/09* | (2010.01) | |
| *C12N 15/88* | (2006.01) | |

(52) U.S. Cl.
CPC .......... *A61K 9/1277* (2013.01); *A61K 31/473* (2013.01); *A61K 31/704* (2013.01); *A61K 38/177* (2013.01); *A61K 48/0033* (2013.01); *C12N 5/0693* (2013.01); *C12N 15/88* (2013.01); *C12N 2501/998* (2013.01); *C12N 2510/02* (2013.01)

(58) Field of Classification Search
CPC .. A61K 31/473; A61K 31/704; A61K 31/711; A61K 35/13; A61K 38/177; A61K 38/19; A61K 45/06; A61K 48/0033; A61K 9/1277; A61K 9/5068; A61K 38/08; A61K 38/10; A61P 35/00; C07K 14/47; C07K 7/06; C07K 7/08; C12N 15/88; C12N 2501/998; C12N 2510/02

See application file for complete search history.

(56) References Cited

U.S. PATENT DOCUMENTS

| 11,230,586 B2 | 1/2022 | Baileykobayashi et al. |
| 11,248,024 B2 * | 2/2022 | Kim ................ C07K 14/4747 |
| 2018/0052150 A1 * | 2/2018 | Klimanskaya ....... G01N 33/582 |

FOREIGN PATENT DOCUMENTS

| JP | 2015-523069 A | 8/2015 |
| JP | 2020-115769 A | 8/2020 |
| KR | 10-2020-0088408 A | 7/2020 |
| KR | 10-2020-0093328 A | 8/2020 |
| WO | WO-2010/50448 A1 | 5/2010 |
| WO | WO-2019/124522 A1 | 6/2019 |

OTHER PUBLICATIONS

Kozaki et al., "Effective modification of cell death-inducing intracelluar peptides by means of a photo-cleavable peptide array-based screening system," Journal of Bioscience and Bioengineering, 2017, 124(2): 209-214. (Year: 2017).*
Nacalai Tesque, Cell Culture Reagents, Medium, pp. 1-6. Accessed Jul. 31, 2024. (Year: 2024).*
Sucorse from Millipore Sigma, pp. 1-7. Accessed Aug. 1, 2024. (Year: 2024).*
Cruickshanks et al., "Lapatinib and obatoclax kill breast cancer cells through reactive oxygen species-dependent endoplasmic reticulum stress," Mol Pharmacol. 82(6):1217-29 (Dec. 2012).
International Search Report and Written Opinion mailed Dec. 14, 2021 for International Application No. PCT/KR2021/006905, Kim et al., "Composition for Promoting Extracellular Vesicle Production Containing Peptide Derived from NOXA Protein and Method for Producing Extracellular Vesicles by Using Same," filed Jun. 3, 2021 (English translation) (19 pages).

(Continued)

*Primary Examiner* — Julie Ha
(74) *Attorney, Agent, or Firm* — Clark & Elbing LLP

(57) ABSTRACT

A method for producing extracellular vesicles (EV) in large quantities by using a peptide derived from Noxa protein, which plays a key role in apoptosis, and derivatives thereof, are described. Also described are the use of the peptide for promoting extracellular vesicle production and methods for producing extracellular vesicles by using the same. The methods of the present invention can efficiently and uniformly be used to mass-produce extracellular vesicles and can be used to produce extracellular vesicles which load drugs that pass poorly through cellular membranes, as well as recombinant proteins or plasmid DNA.

5 Claims, 36 Drawing Sheets

Specification includes a Sequence Listing.

(56) References Cited

OTHER PUBLICATIONS

Kakarla et al., "Apoptotic cell-derived exosomes: messages from dying cells," Experimental & Molecular Medicine. 52(1):1-6 (Jan. 2020).
Kim et al., "Minimal killing unit of the mitochondrial targeting domain of Noxa," J Pept Sci. 19(8):485-490 (Epub Jun. 2013).
Kim, Jeong-Mi, Thesis: "Characteristics of Exosomes released from caspasedependent cell deaths," Master, Department of Biomedical Sciences, Graduate School of Ajou University (2017) (60 pages).
Office Action dated Feb. 14, 2024 for Japanese Patent Application No. JP 2023-507310, Kim et al., "Composition for Promoting Extracellular Vesicle Production Containing Peptide Derived from NOXA Protein and Method for Producing Extracellular Vesicles by Using Same," filed Jun. 3, 2021 (English translation) (11 pages).
Office Action dated Jun. 26, 2024 for Japanese Patent Application No. JP 2023-507310, Kim et al., "Composition for Promoting Extracellular Vesicle Production Containing Peptide Derived from NOXA Protein and Method for Producing Extracellular Vesicles by Using Same," filed Jun. 3, 2021 (English translation) (10 pages).
Office Action dated Mar. 30, 2022 for Korean Patent Application No. KR 10-2020-0115145, Kim et al., "Noxa Composition for Promoting the Production of Extracellular Vesicles Containing A Peptide Derived from NOXA Protein and A Method for Producing Extracellular Vesicles Using the Same," filed Sep. 9, 2020 (English translation) (11 pages).
Seo et al., "The cell death-inducing activity of the peptide containing Noxa mitochondrial-targeting domain is associated with calcium release," Cancer Res. 69(21):8356-65 (Nov. 2009).
Lim et al., "Rapid production method with increased yield of high-purity extracellular vesicles obtained using extended mitochondrial targeting domain peptide," J Extracell Vesicles. 11(10):e12274 (Oct. 2022) (17 pages).

* cited by examiner

[Fig 1]
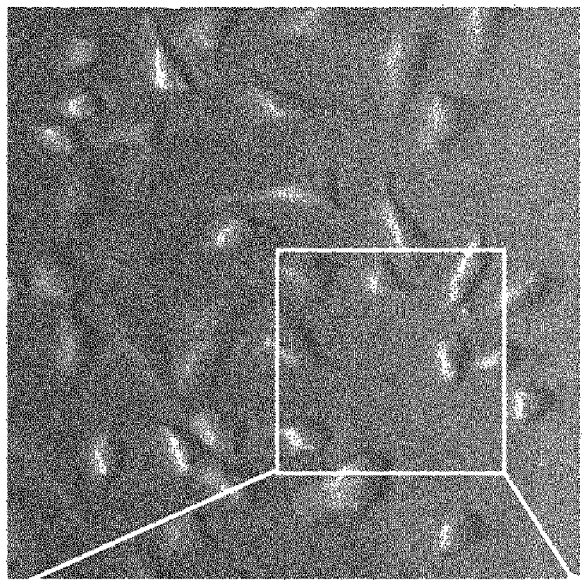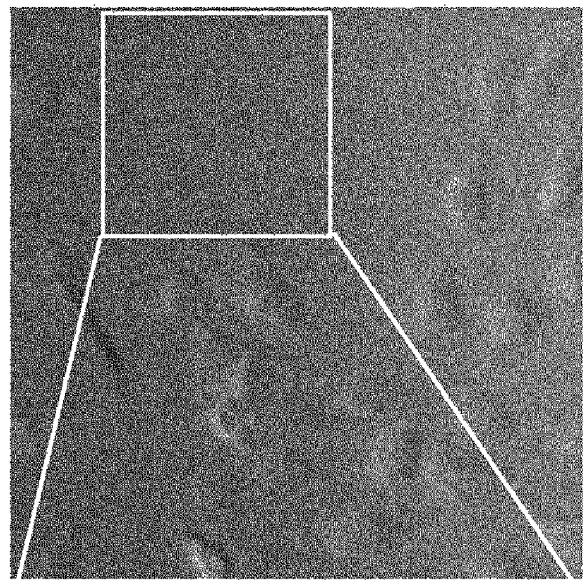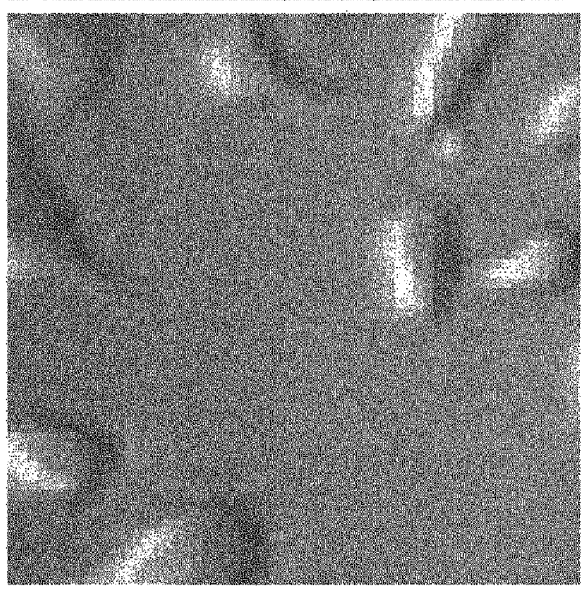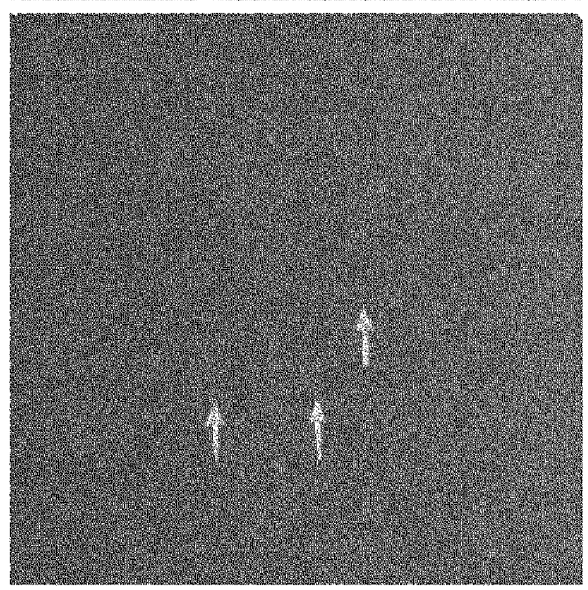
Control      eMTDΔ4

[Fig 2a]
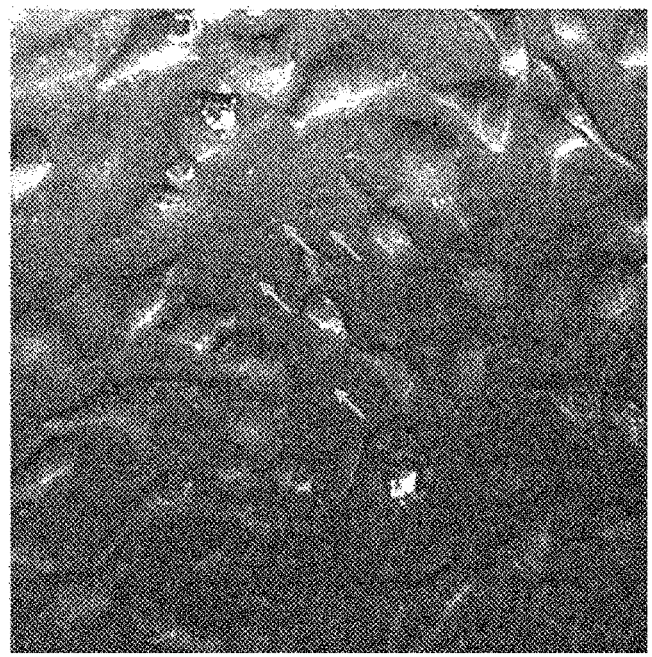
R(8):MTD
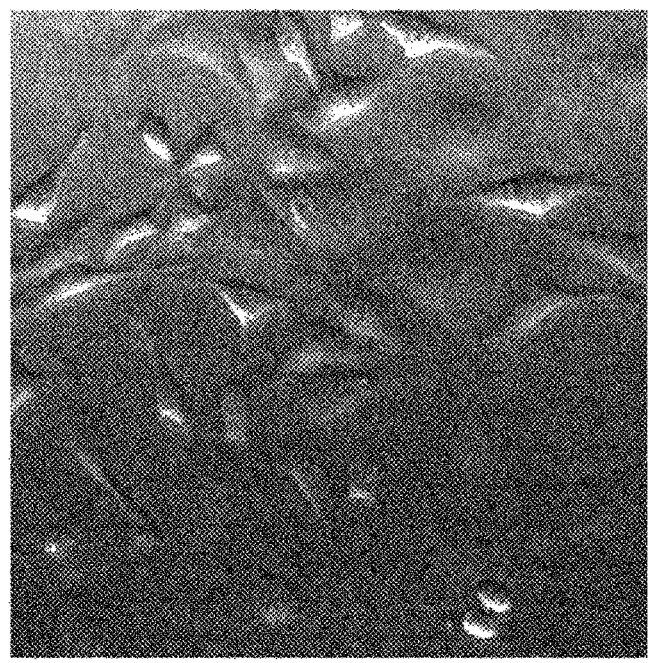
None
Buffer 1

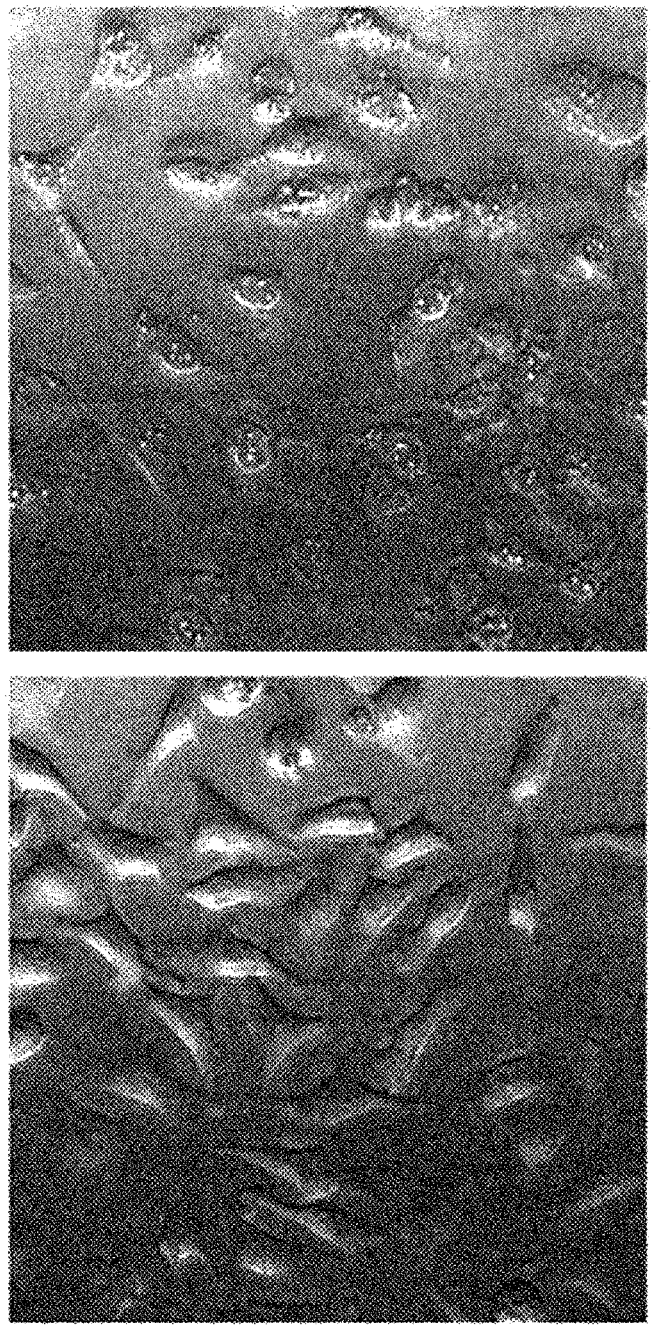

[Fig 2c]
R(8):MTD
None
Buffer 3

[Fig 2d]
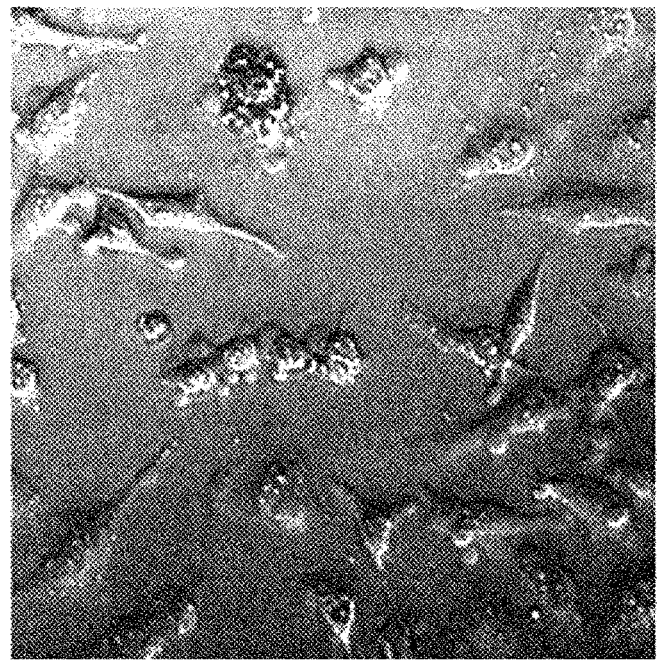
R(8):MTD
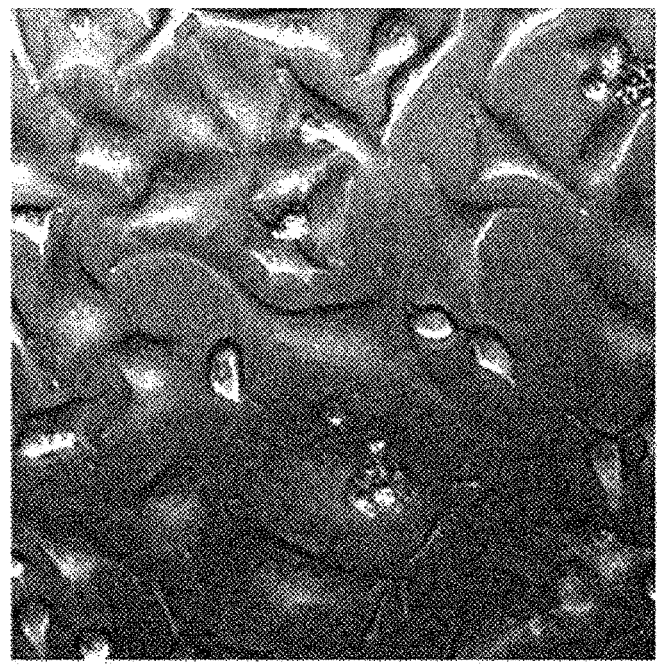
None
Buffer 4

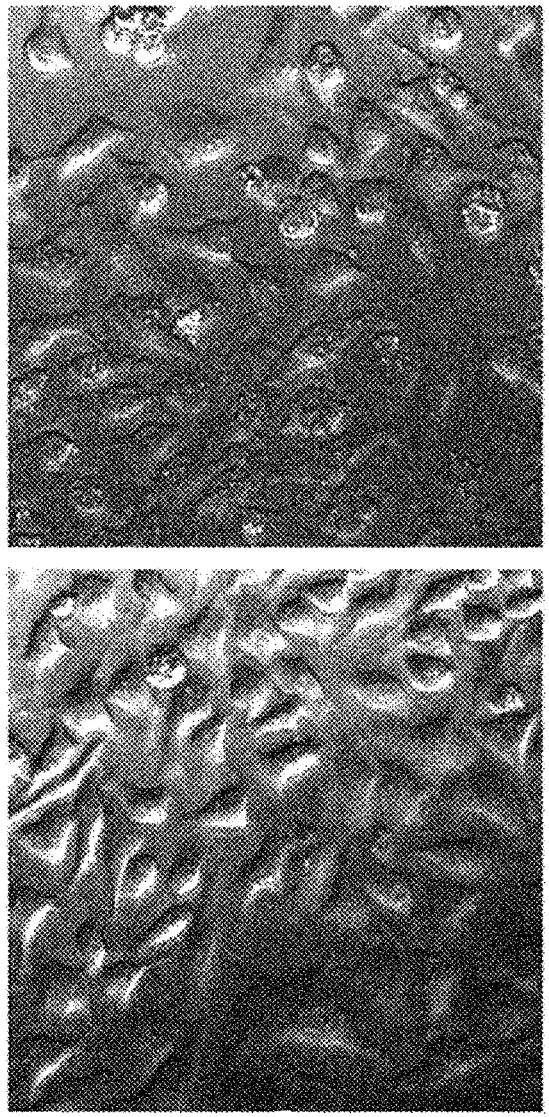
[Fig 2e]

[Fig 2f]
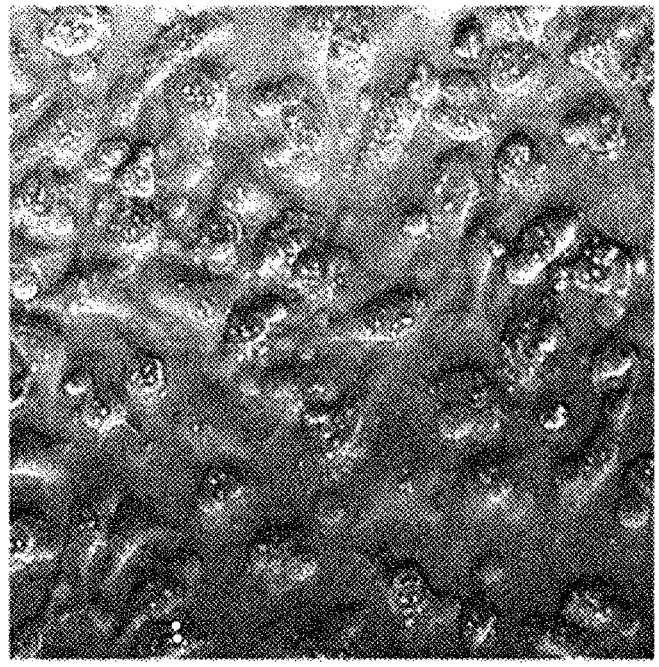
R(8):MTD
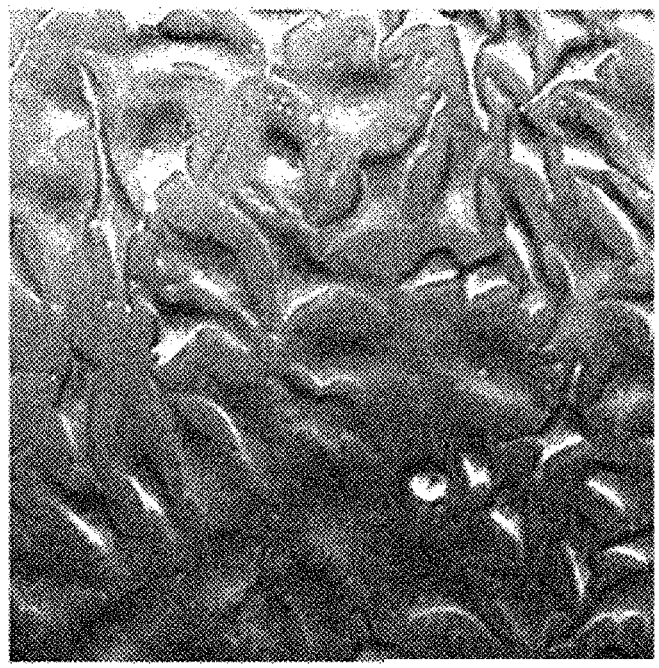
None
Buffer 6

[Fig 2g]
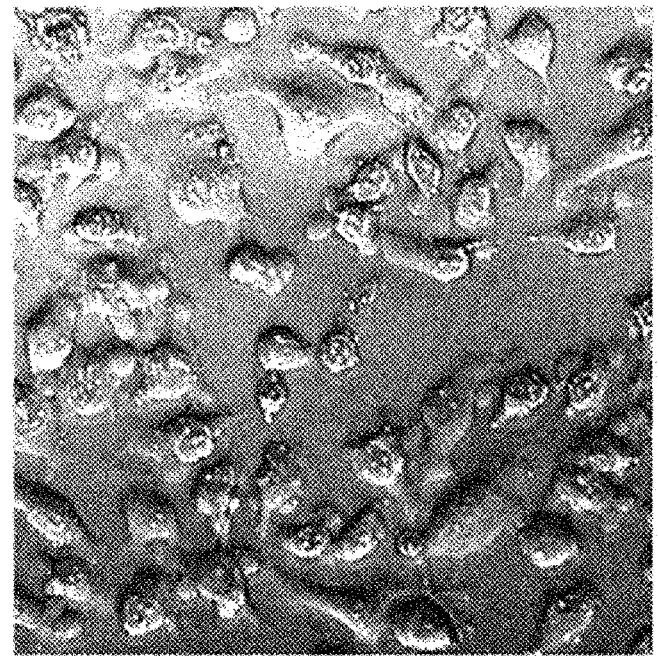
R(8):MTD
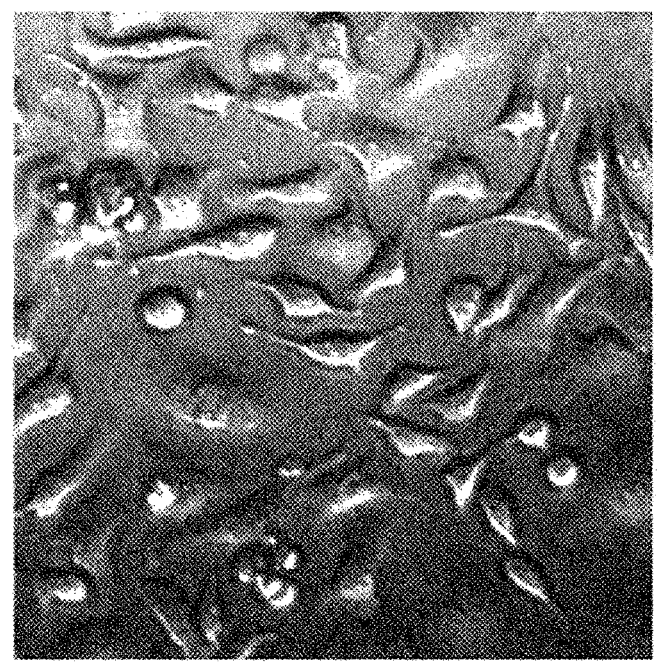
None
Buffer 7

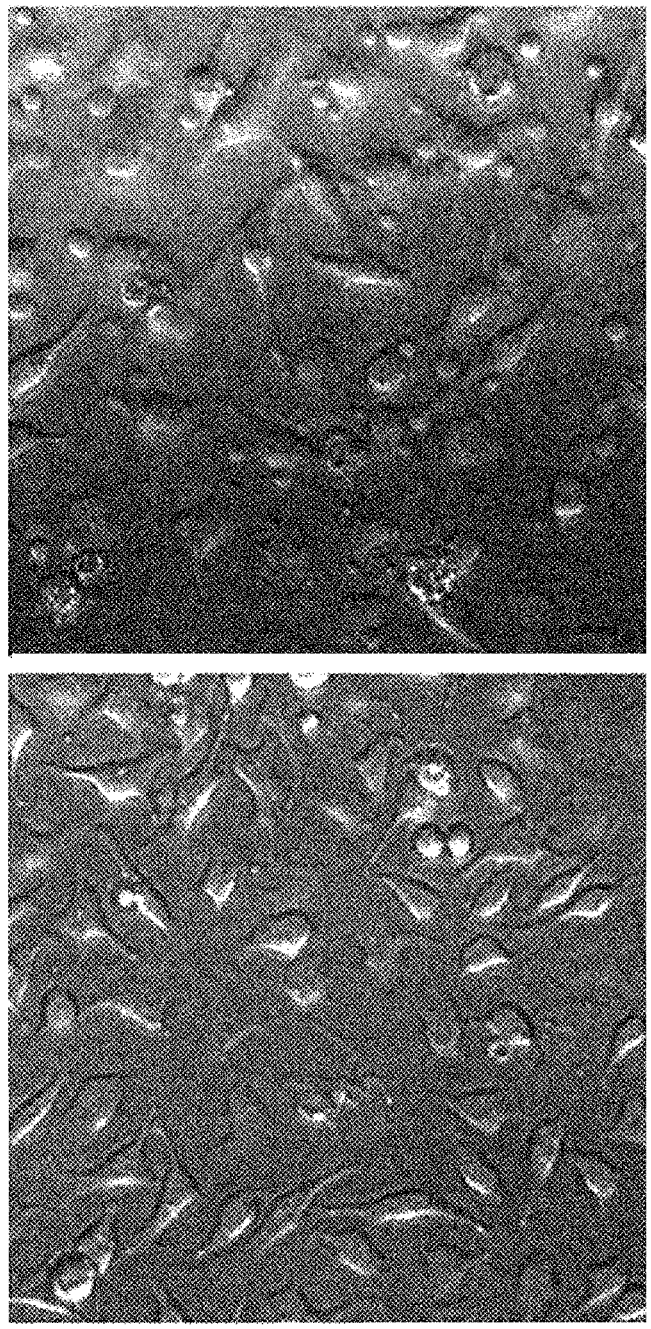
[Fig 2h]

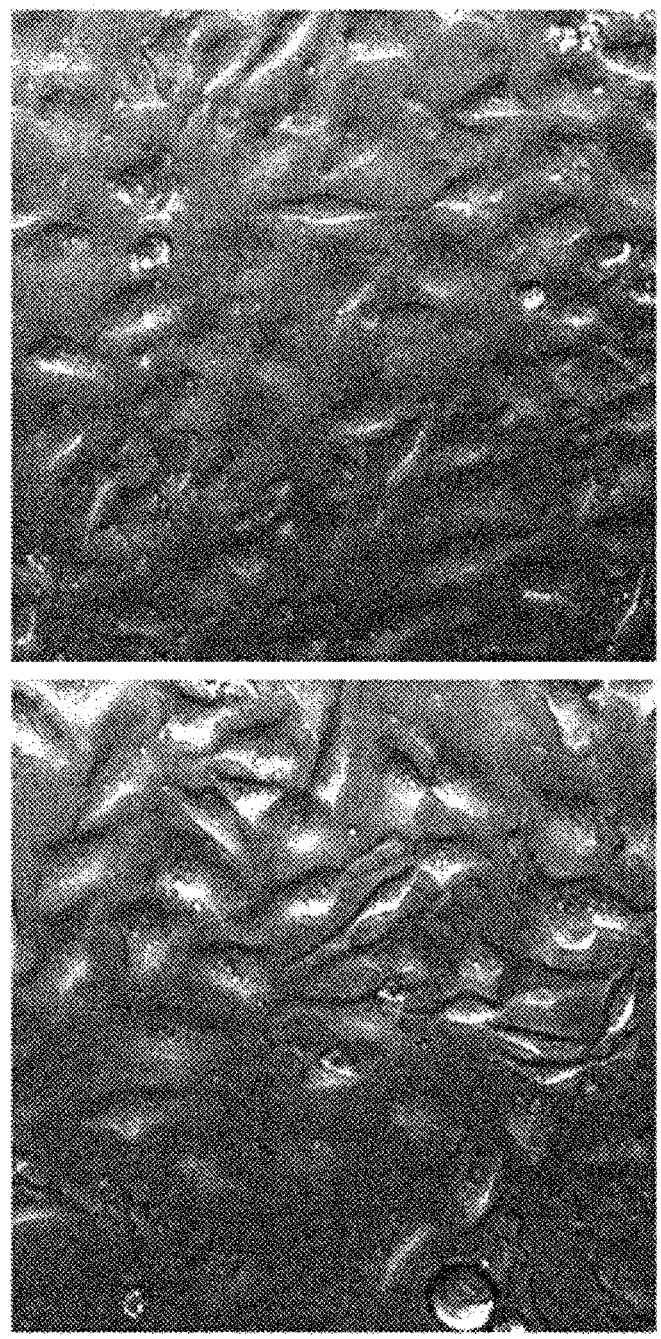
[Fig. 2i]

[Fig 2j]
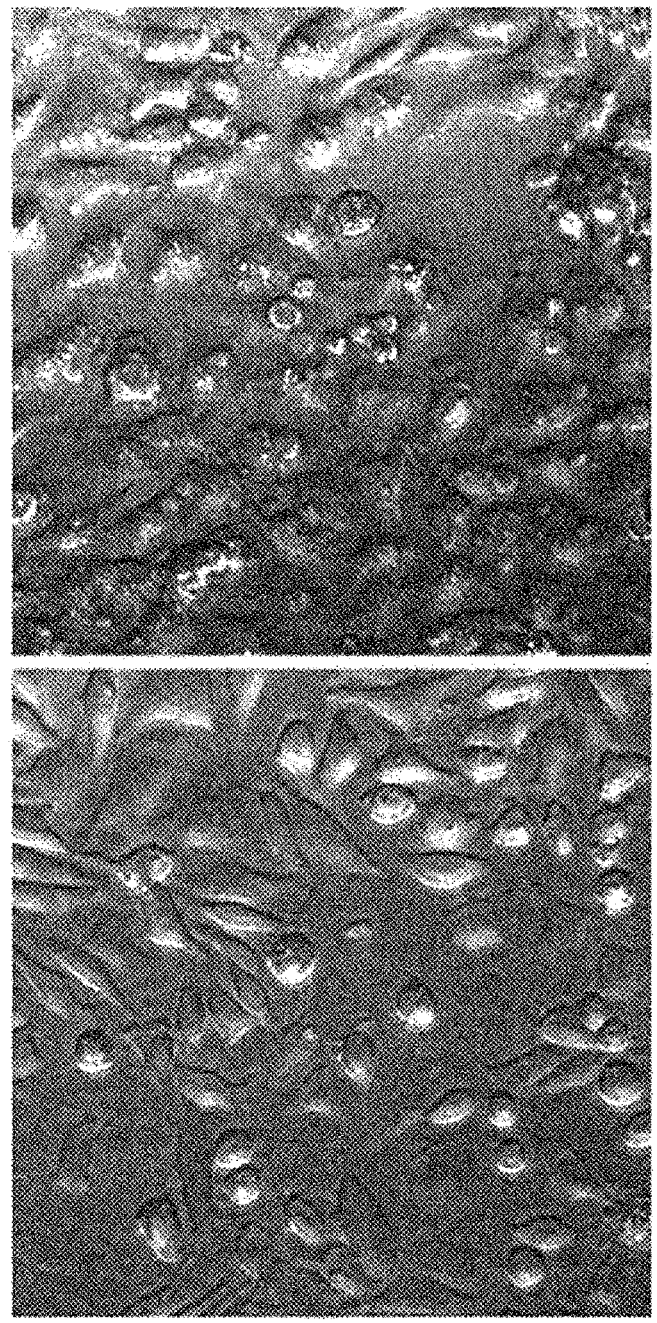

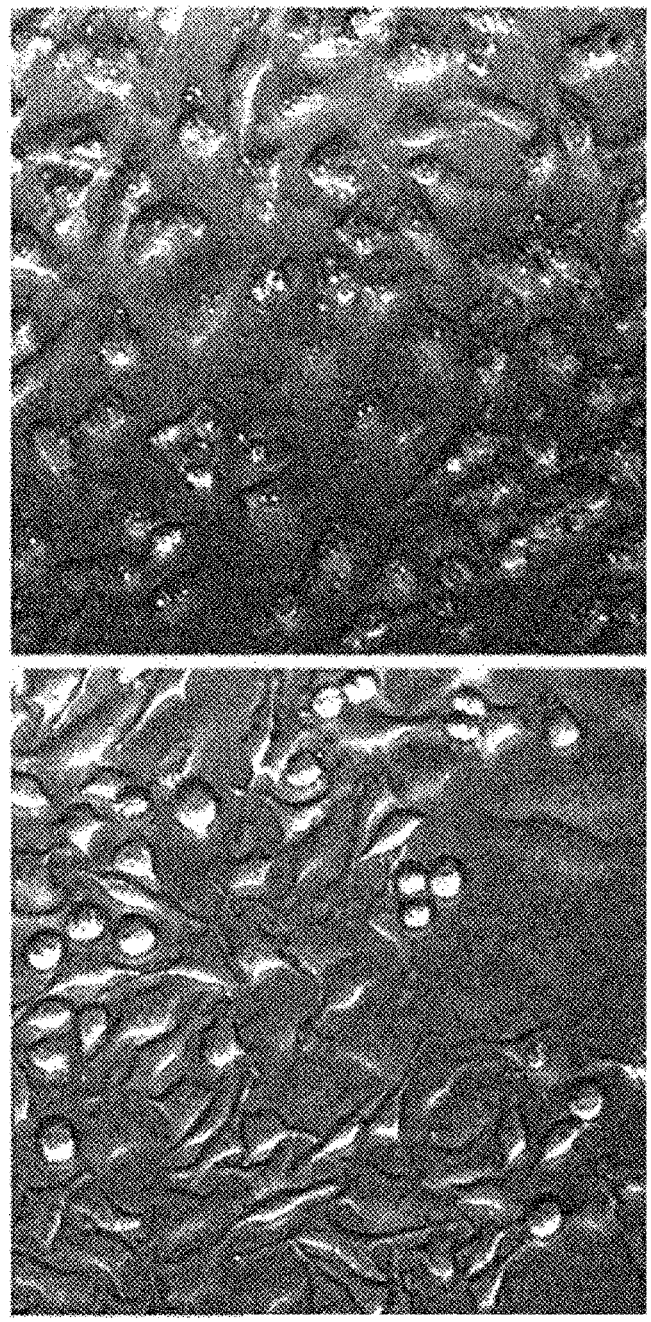
[Fig 2k]

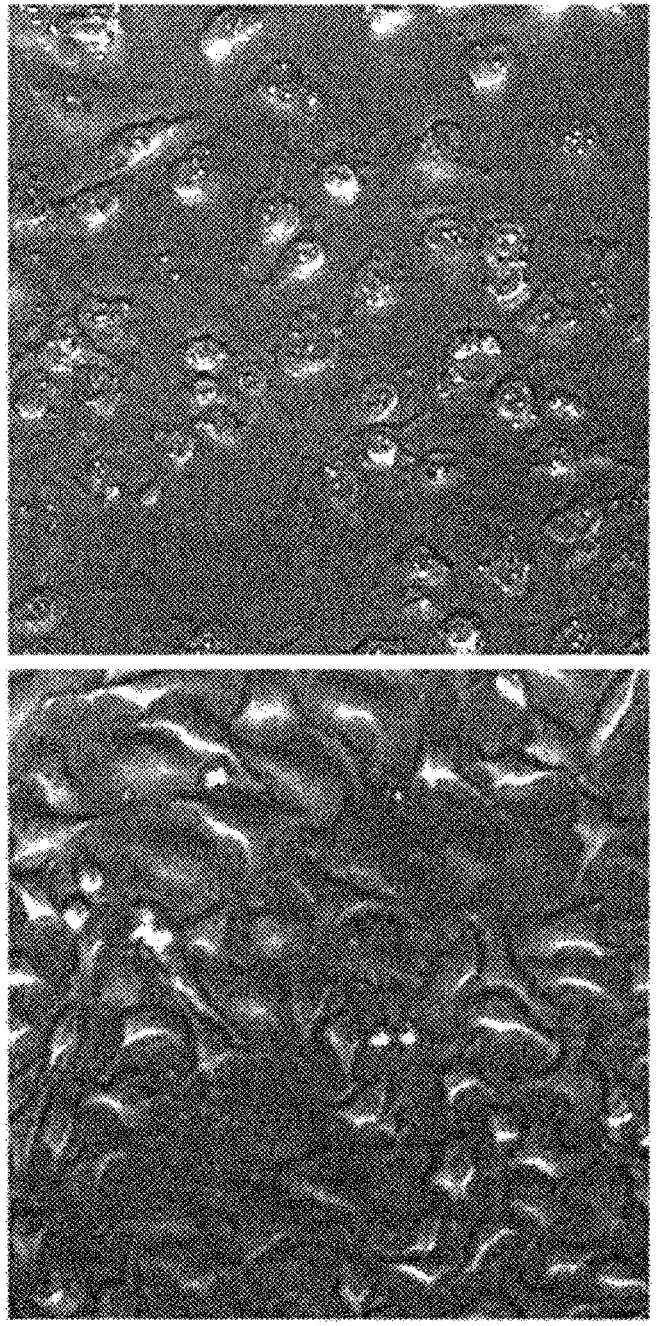
[Fig 21]

[Fig 2m]
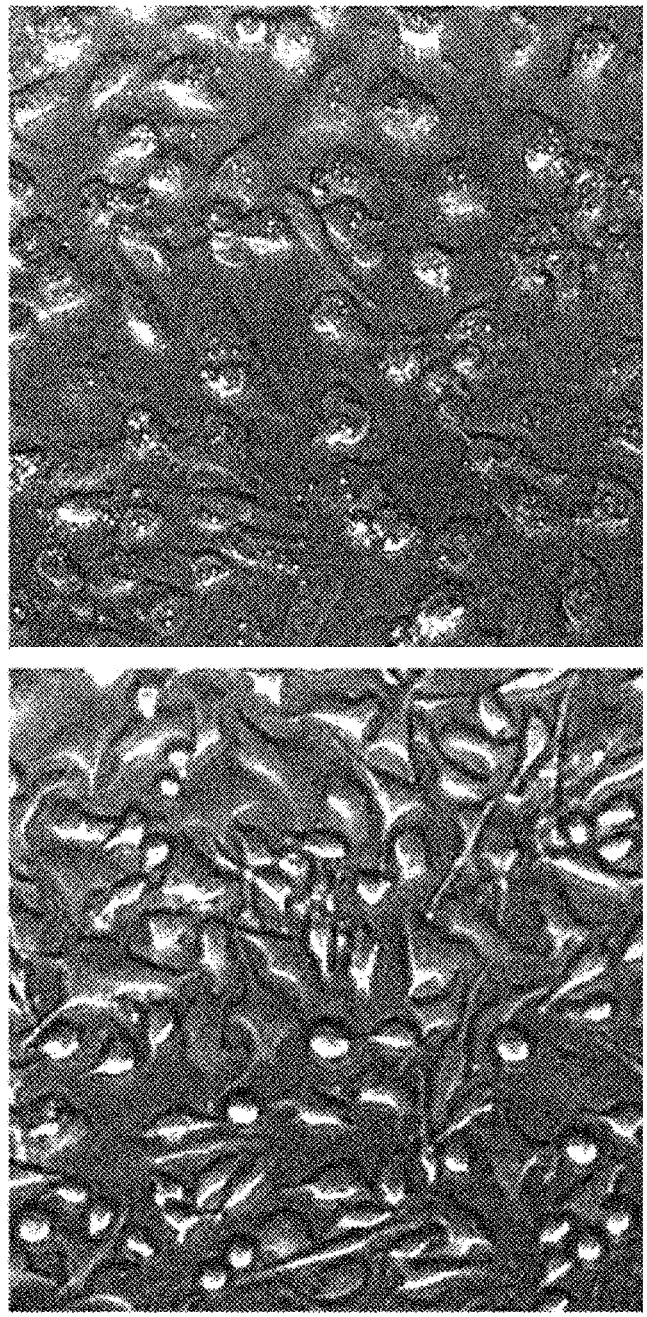

[Fig 2n]
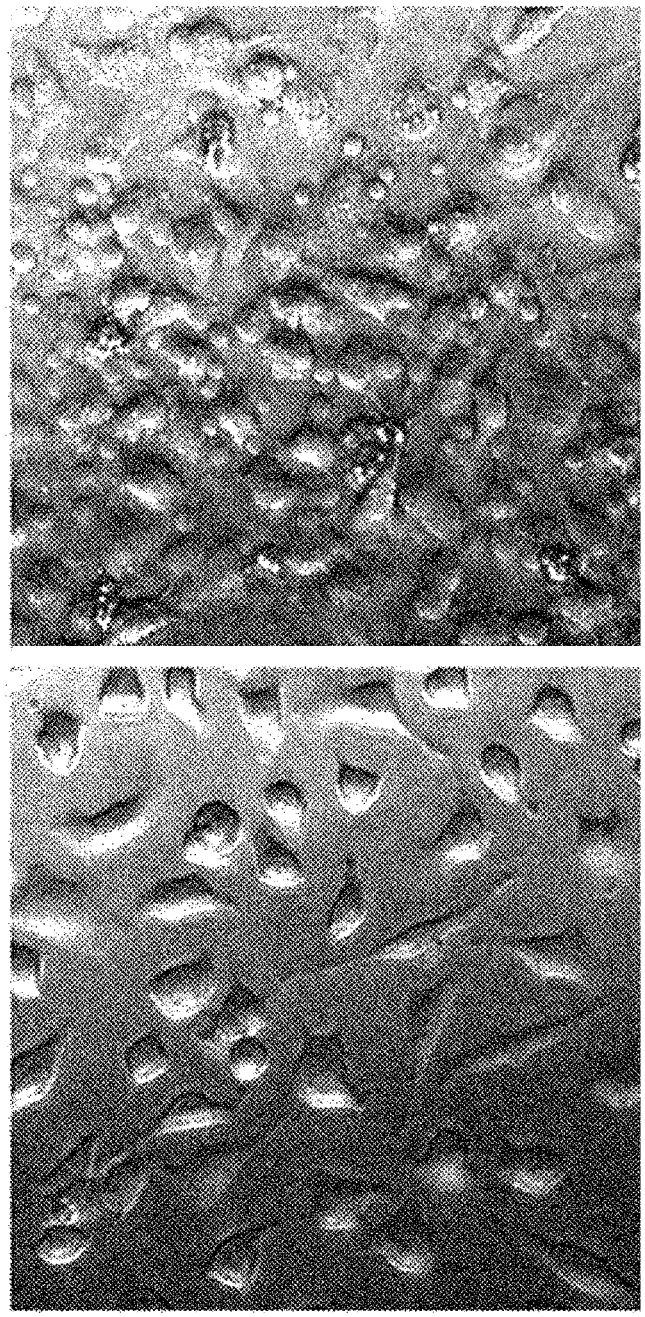

[Fig. 20]
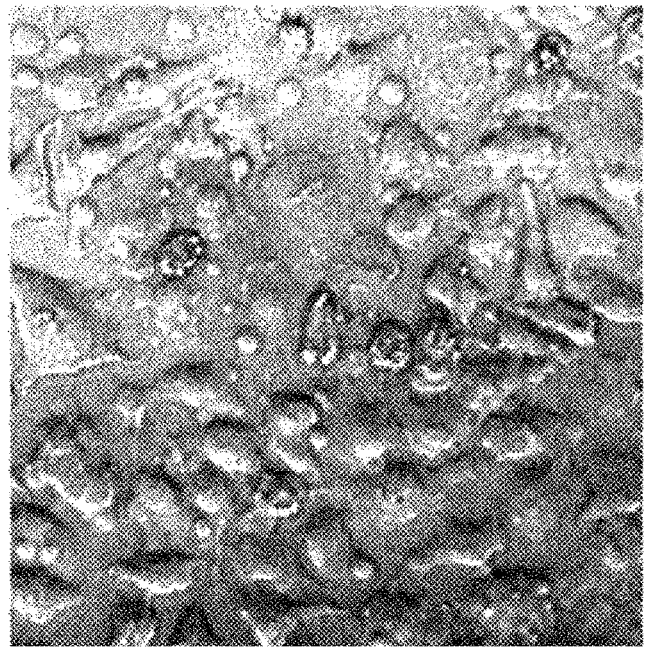
R(8):MTD
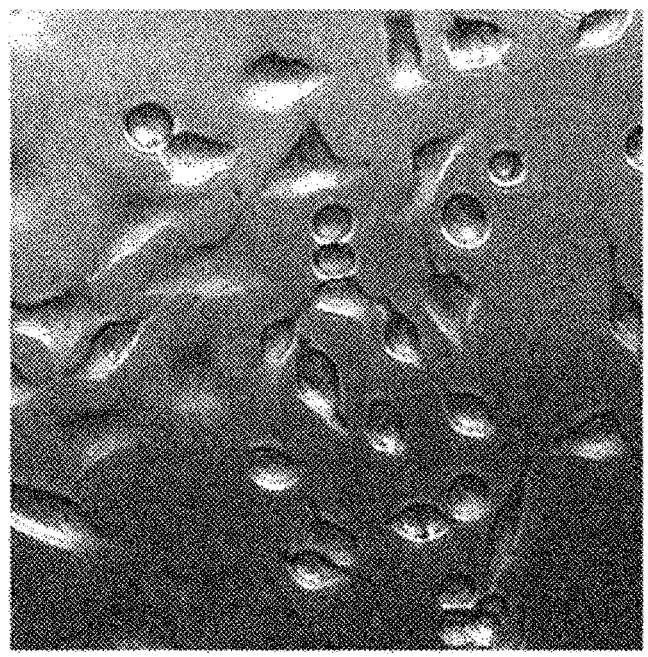
None
Buffer 15

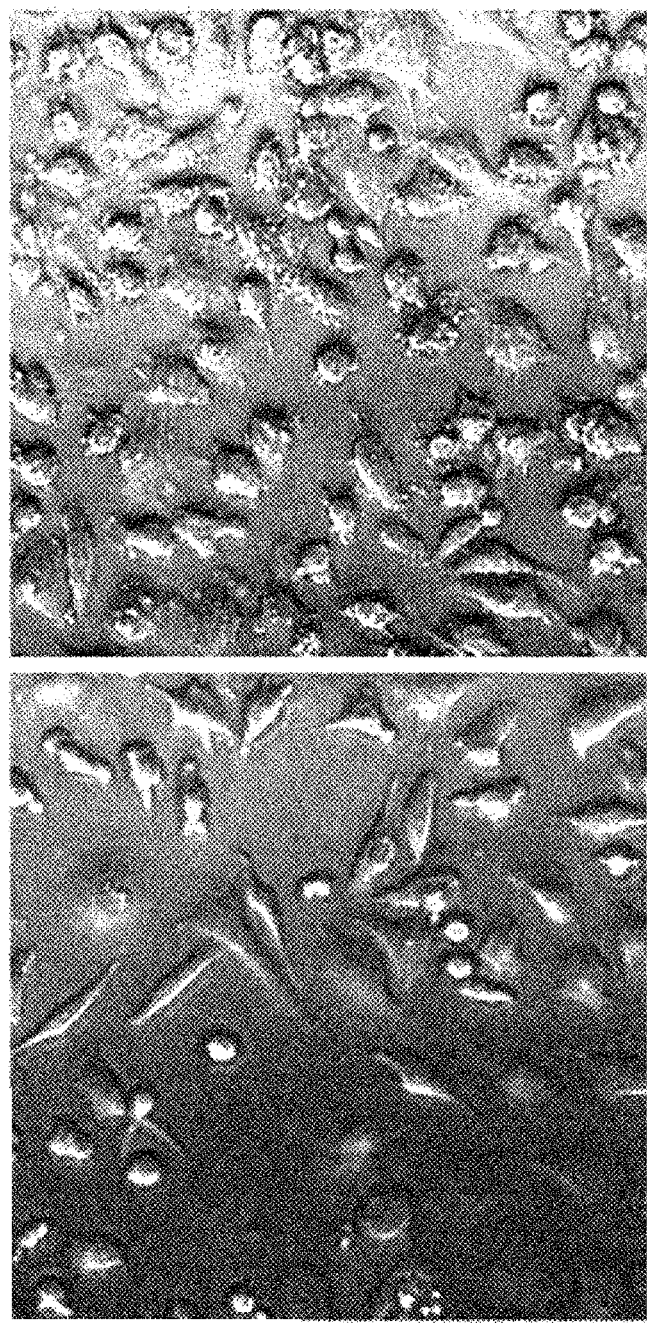
[Fig 2p]

[Fig 2q]
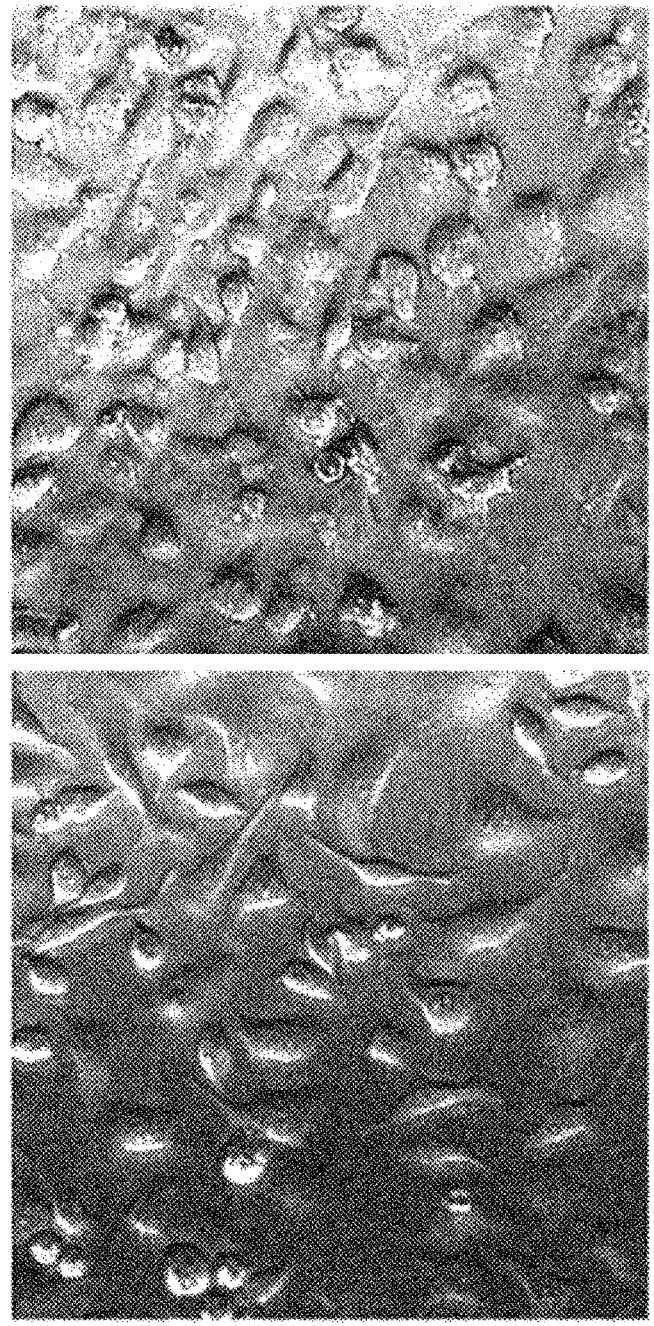

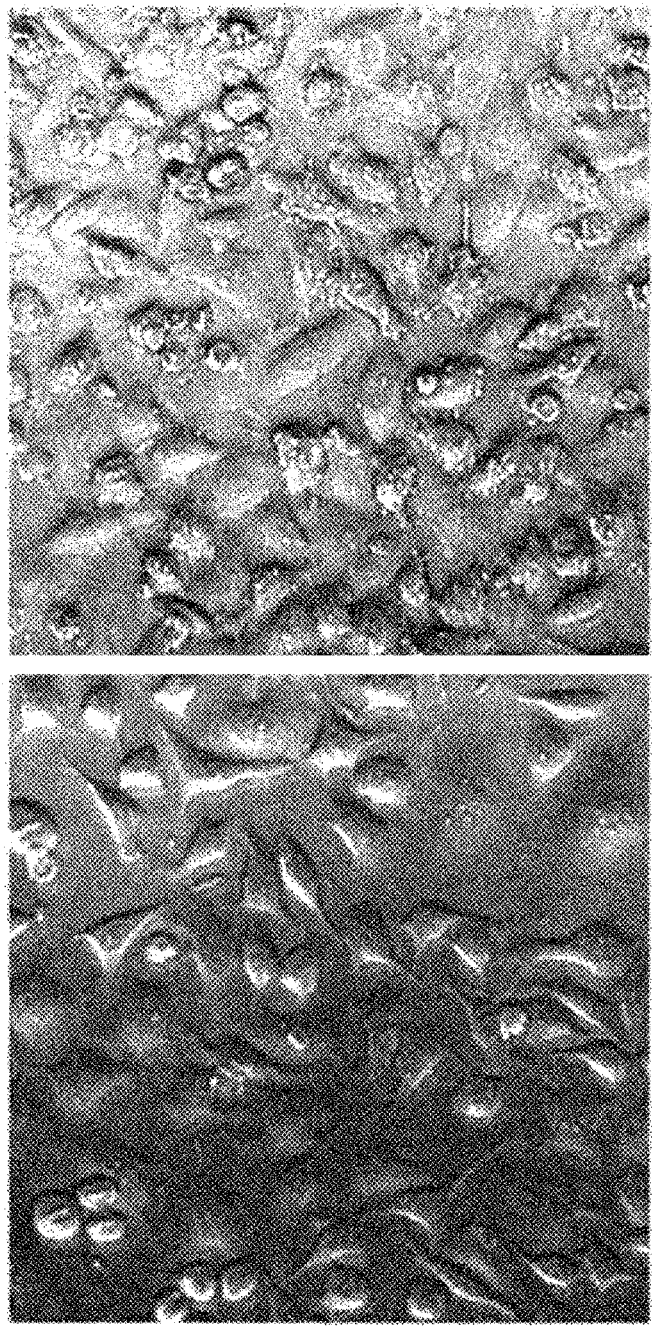
[Fig 2r]

[Fig 2s]
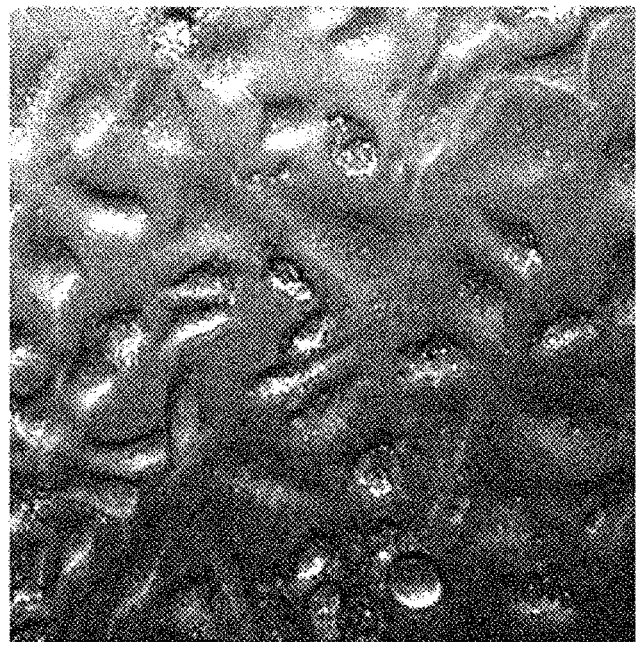
R(8):MTD
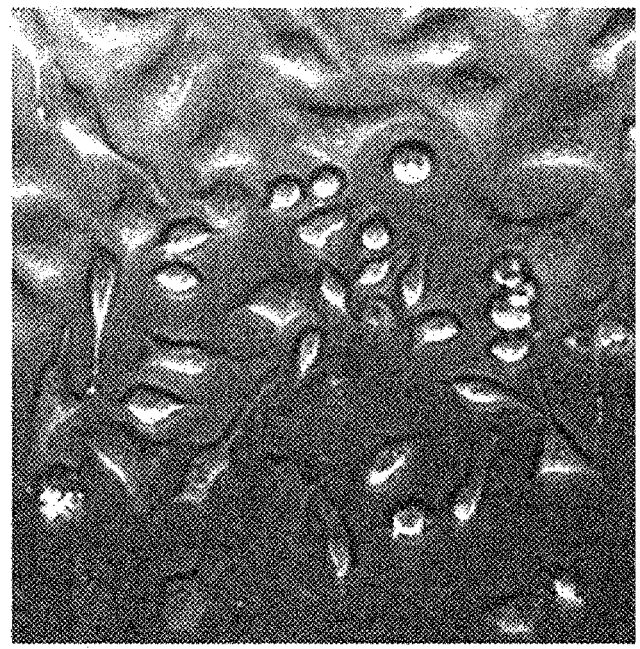
None
Buffer 19

[Fig 3a]
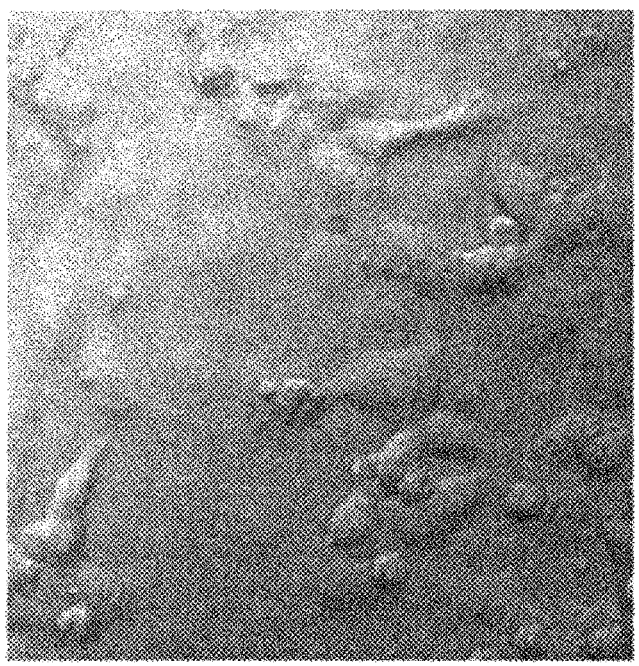

[Fig 3b]
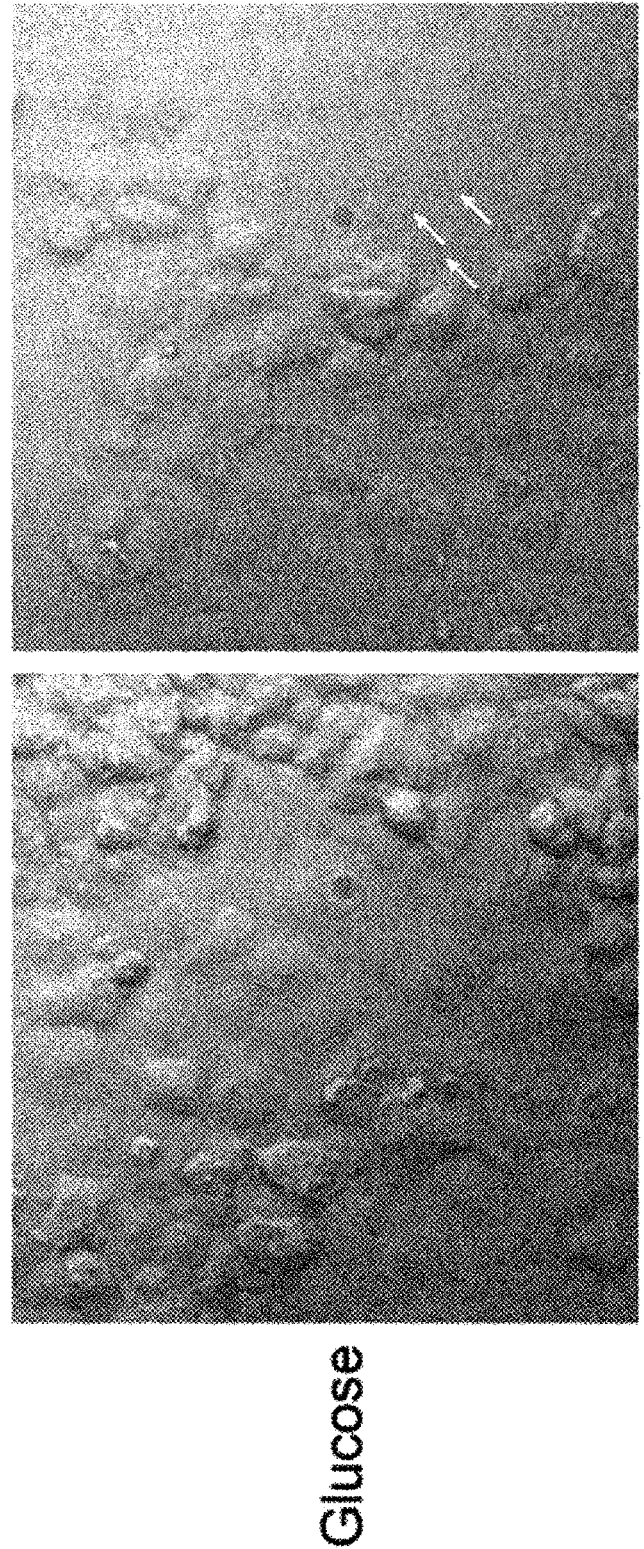

[Fig 3c]
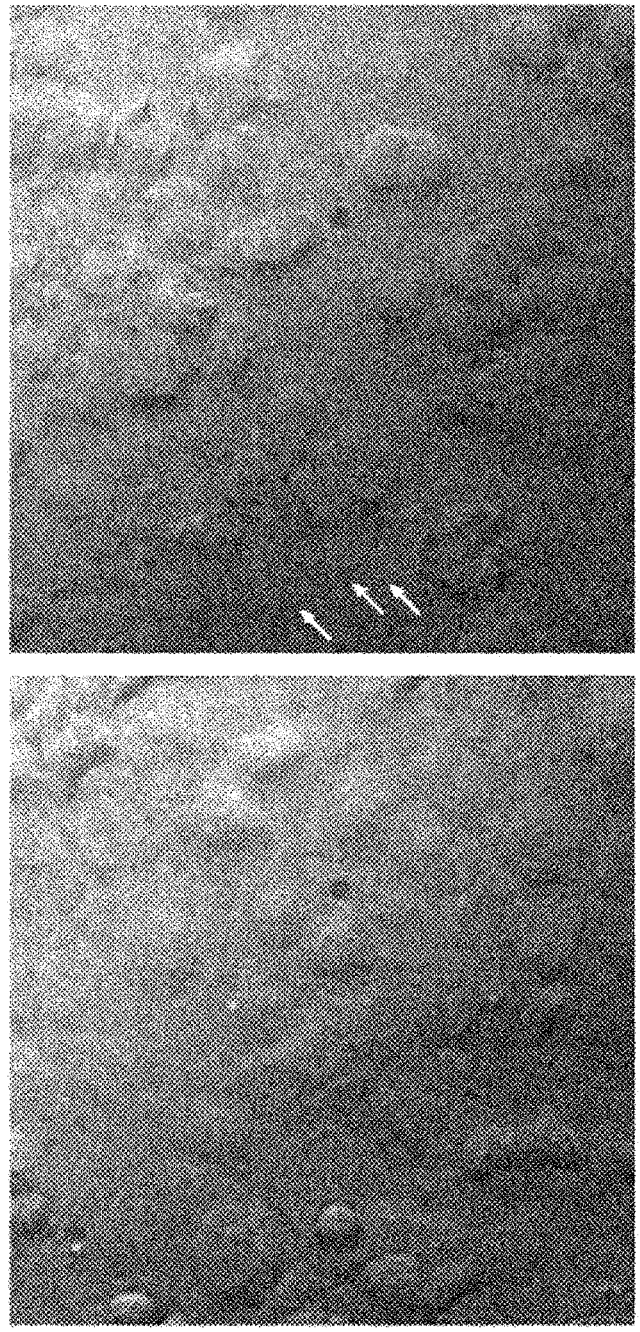

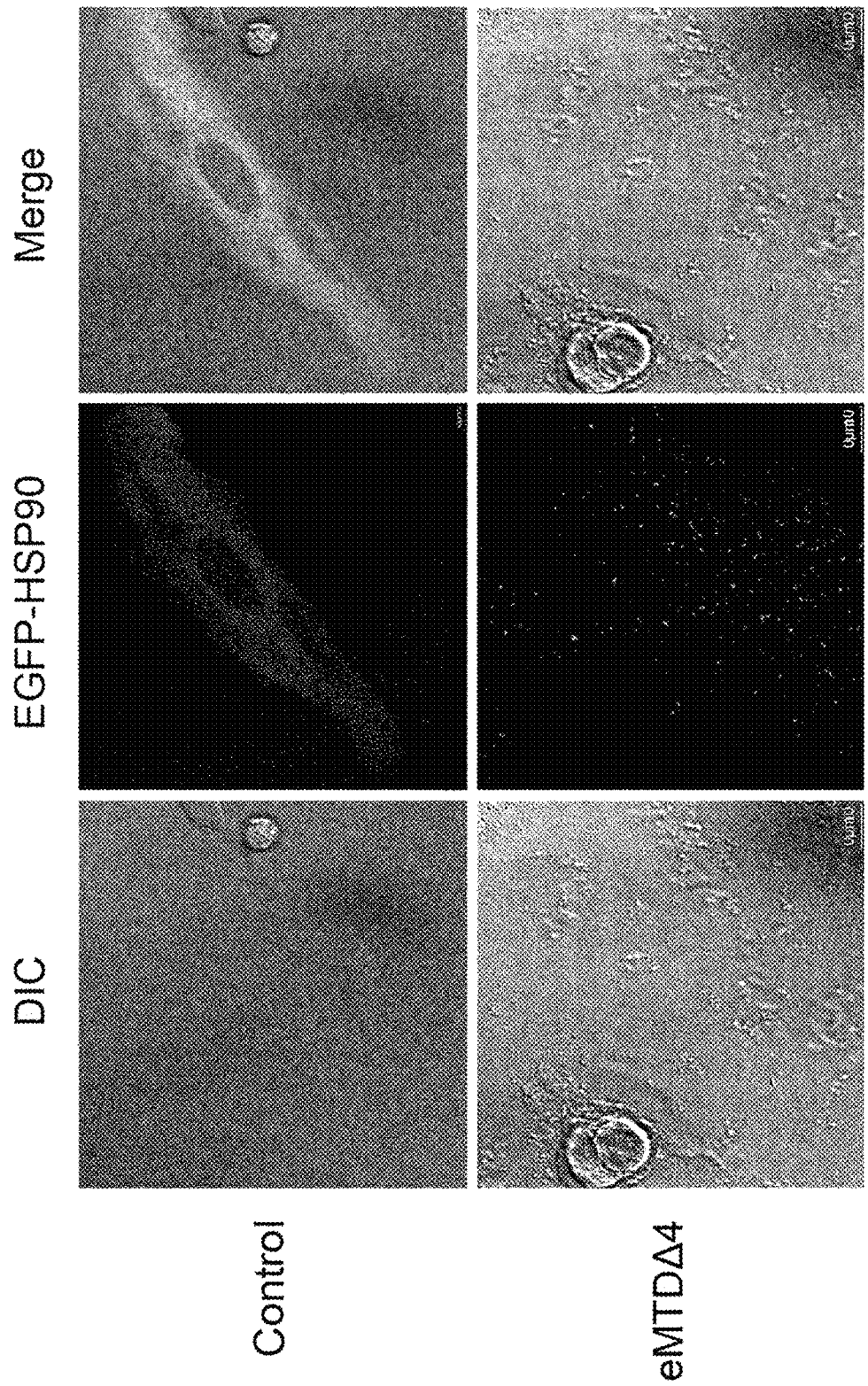

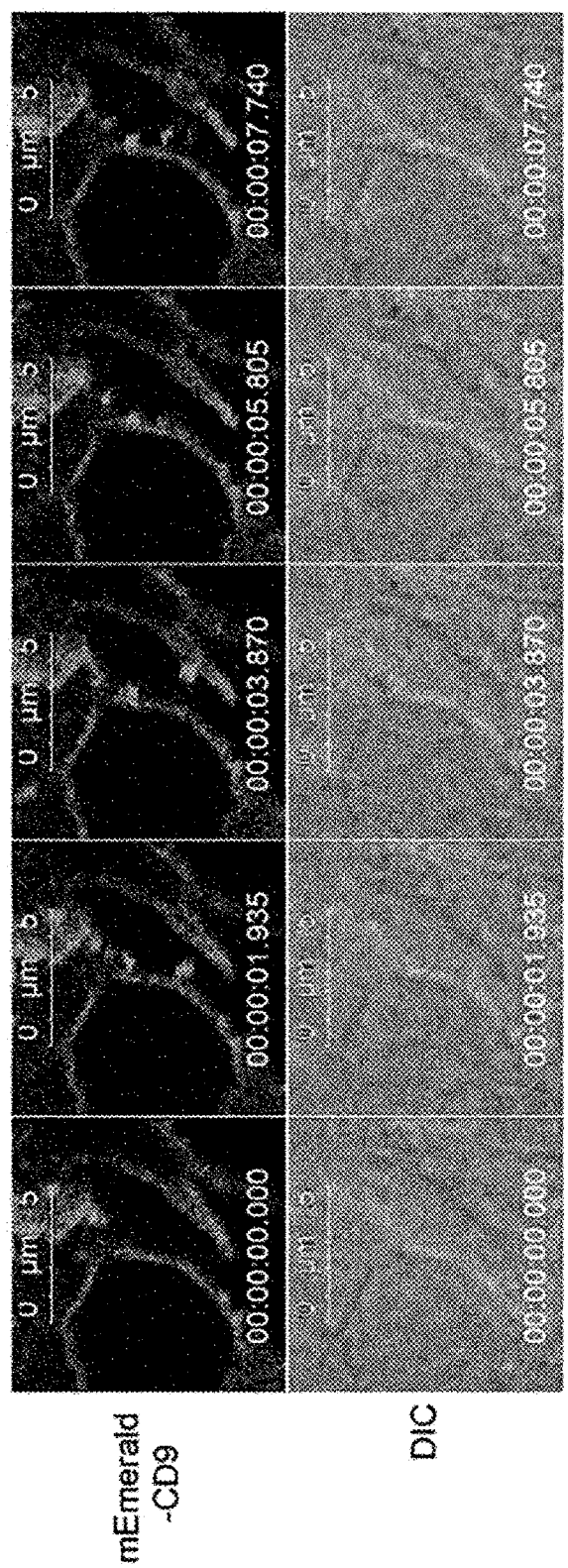

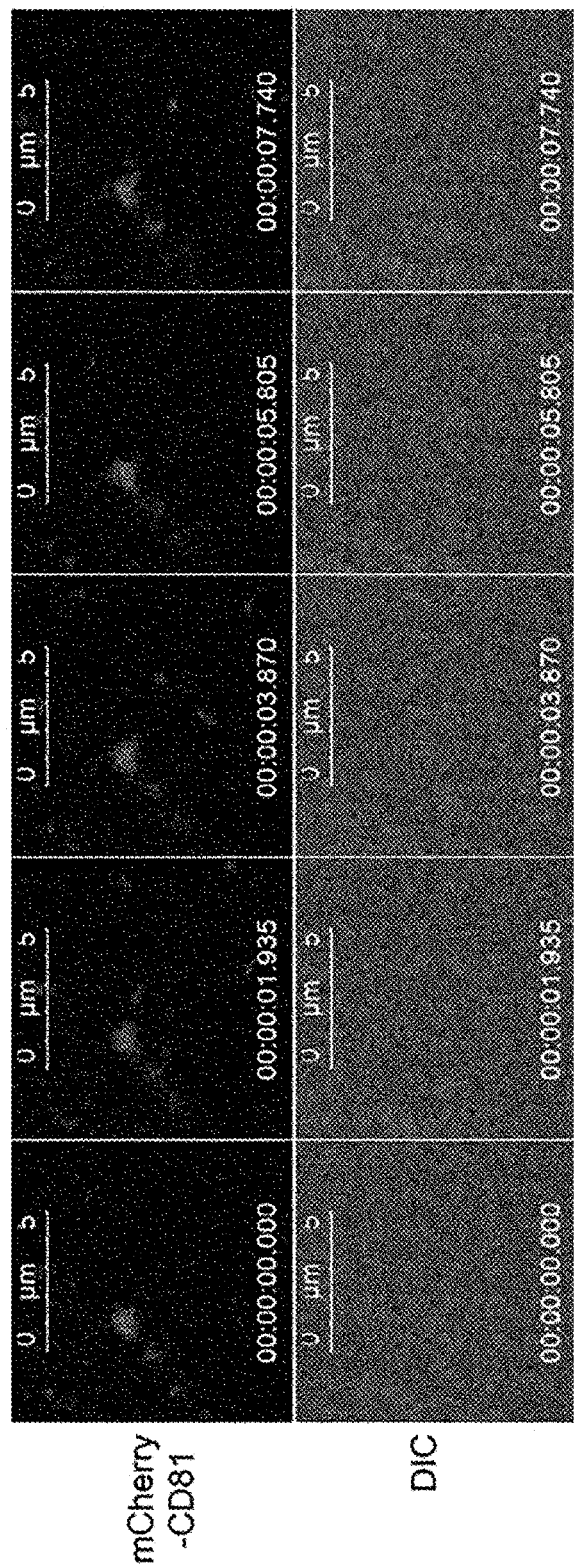
[Fig 5b]

[Fig 6a]
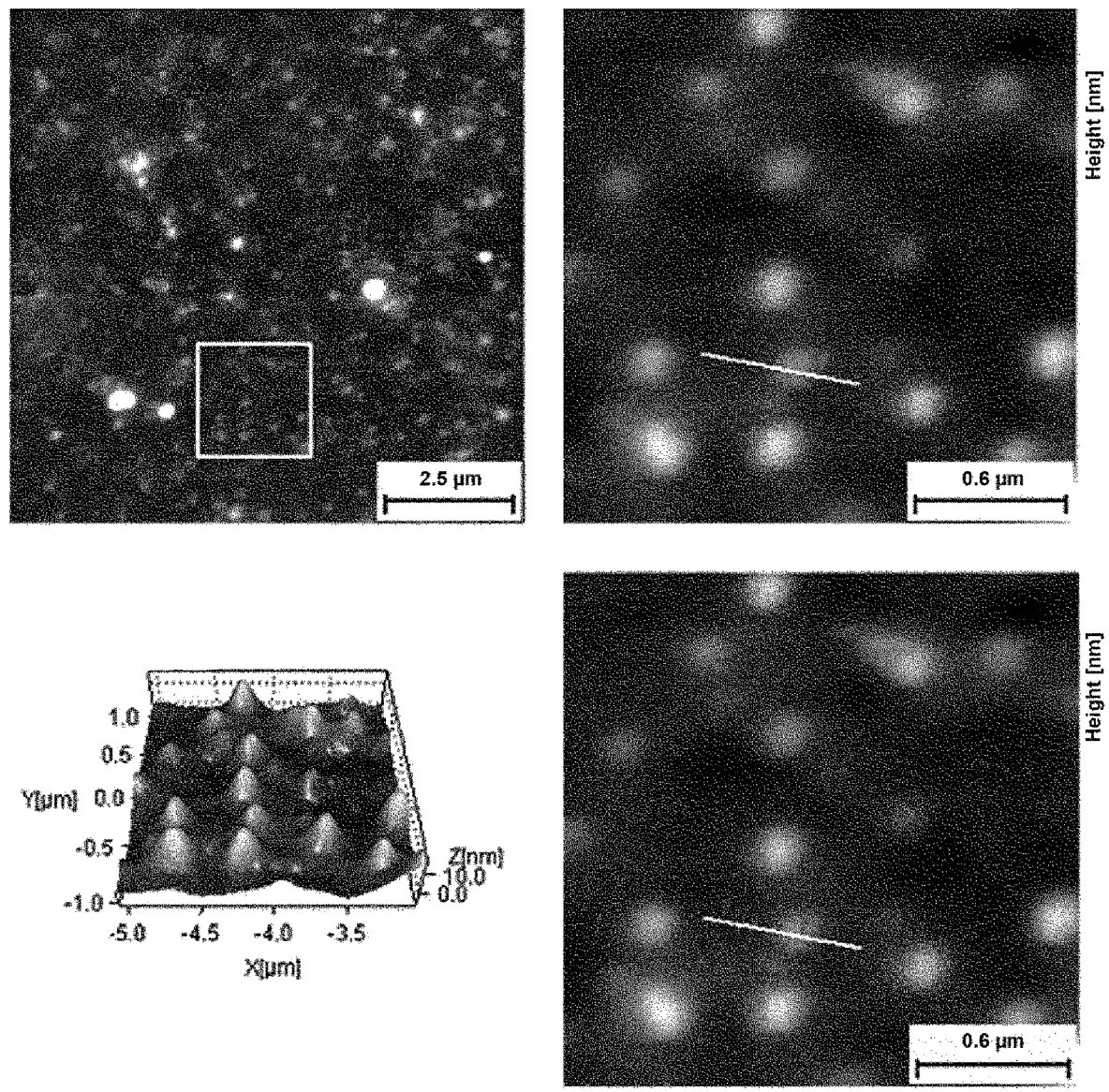

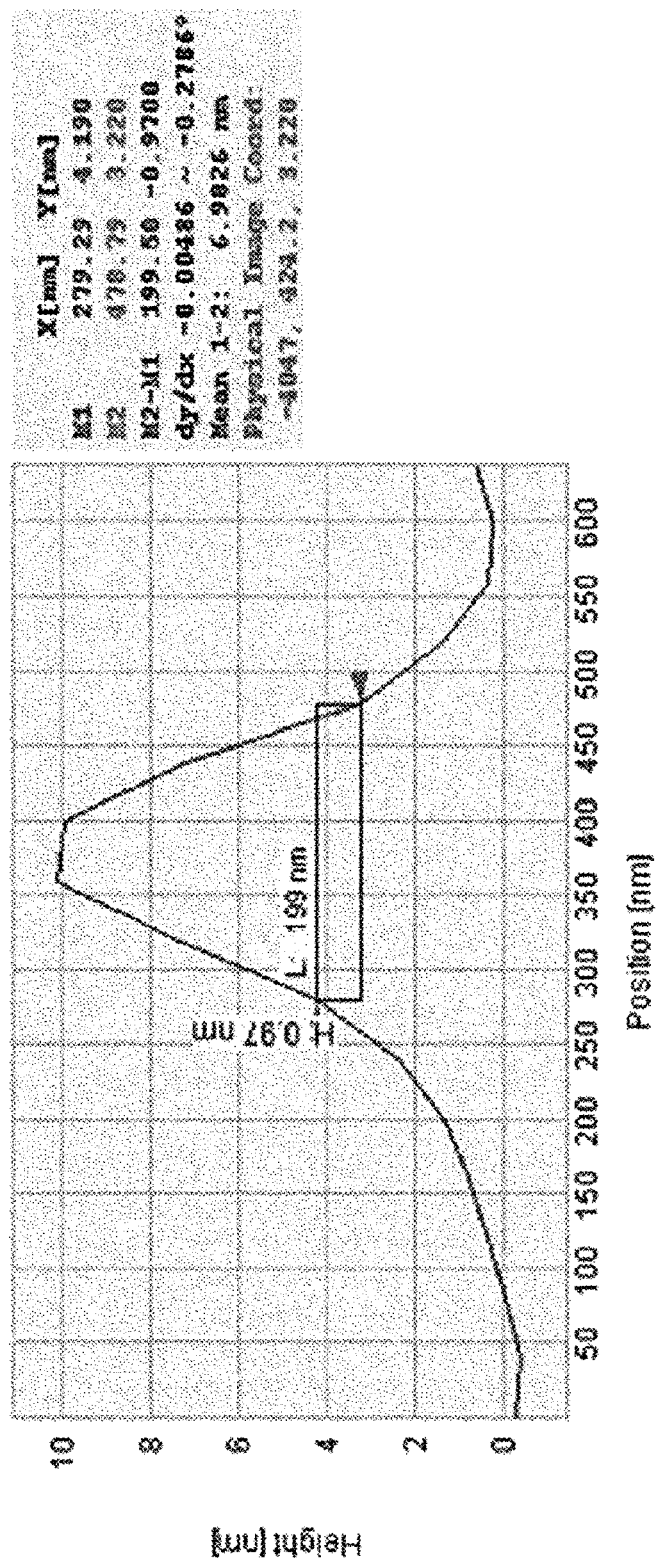
[Fig 6b]

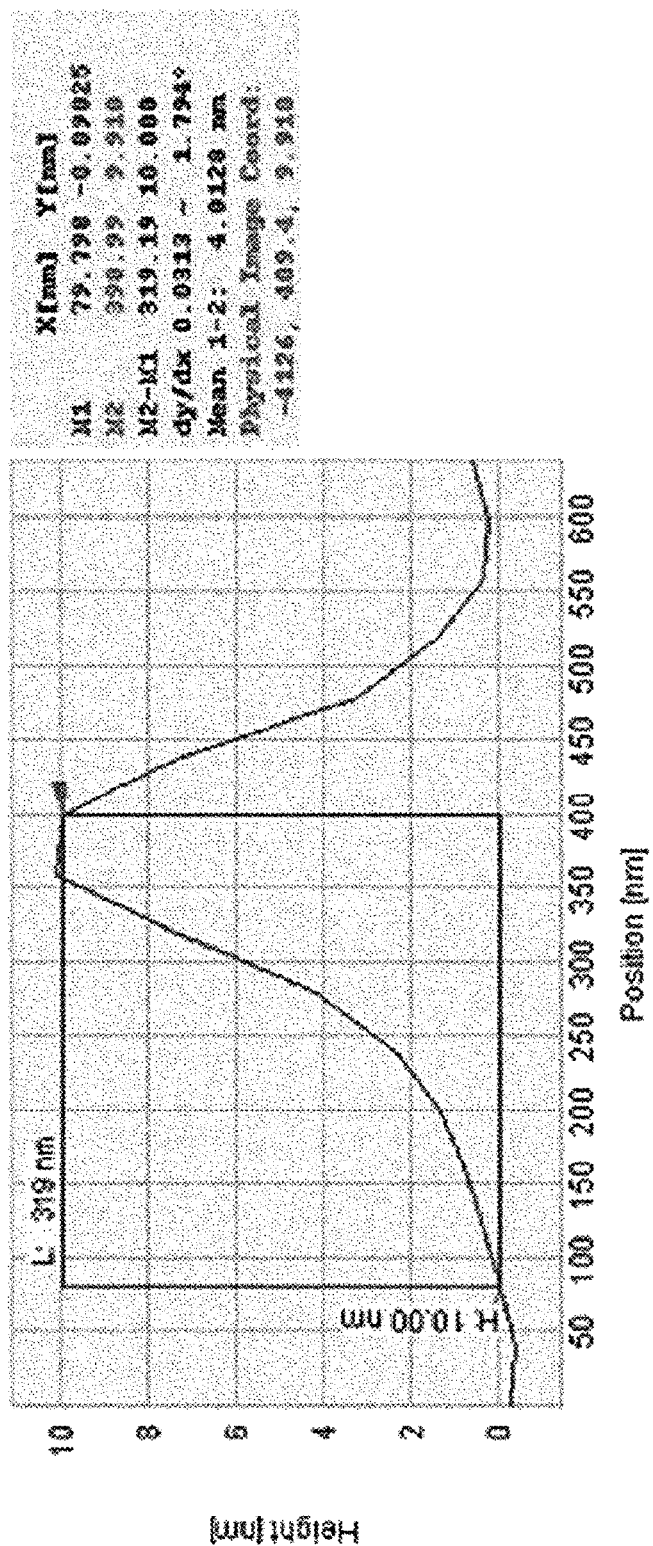
[Fig 6c]

[Fig 7]
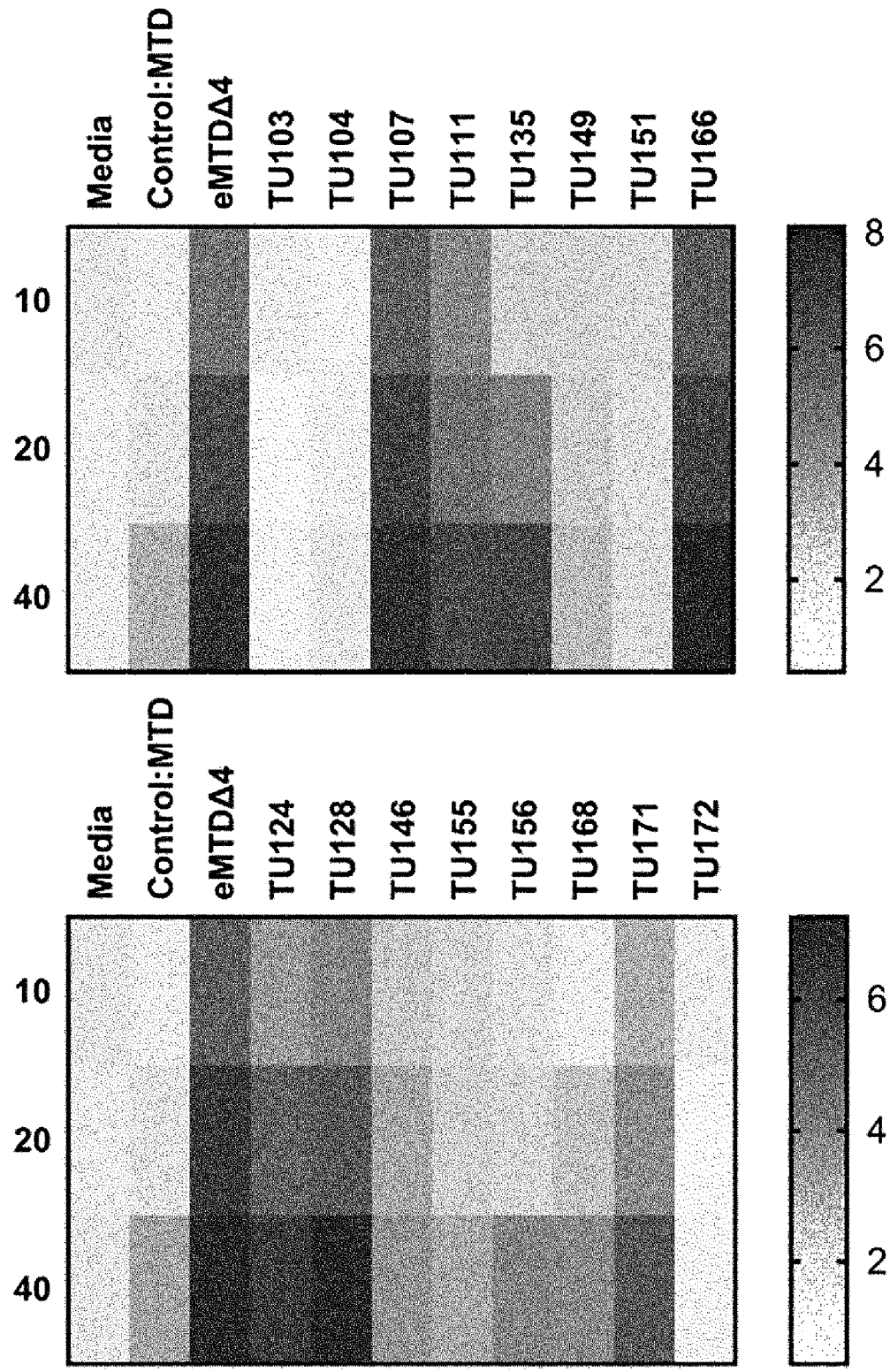

[Fig 8a]
MTD
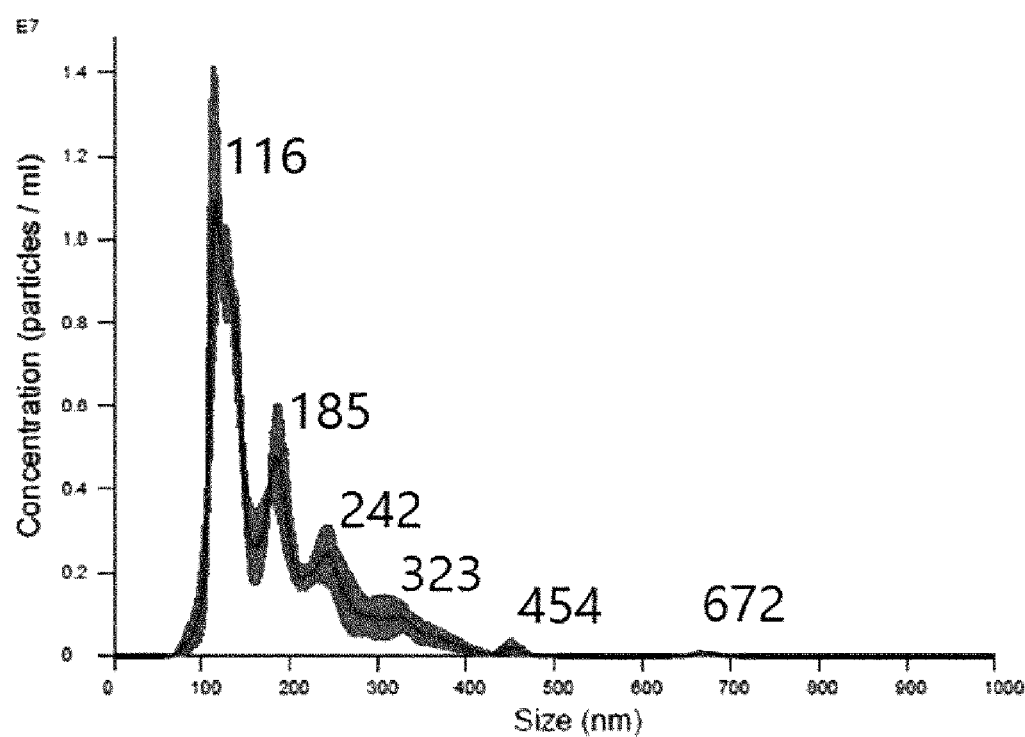

[Fig 8b]
eMTDΔ4
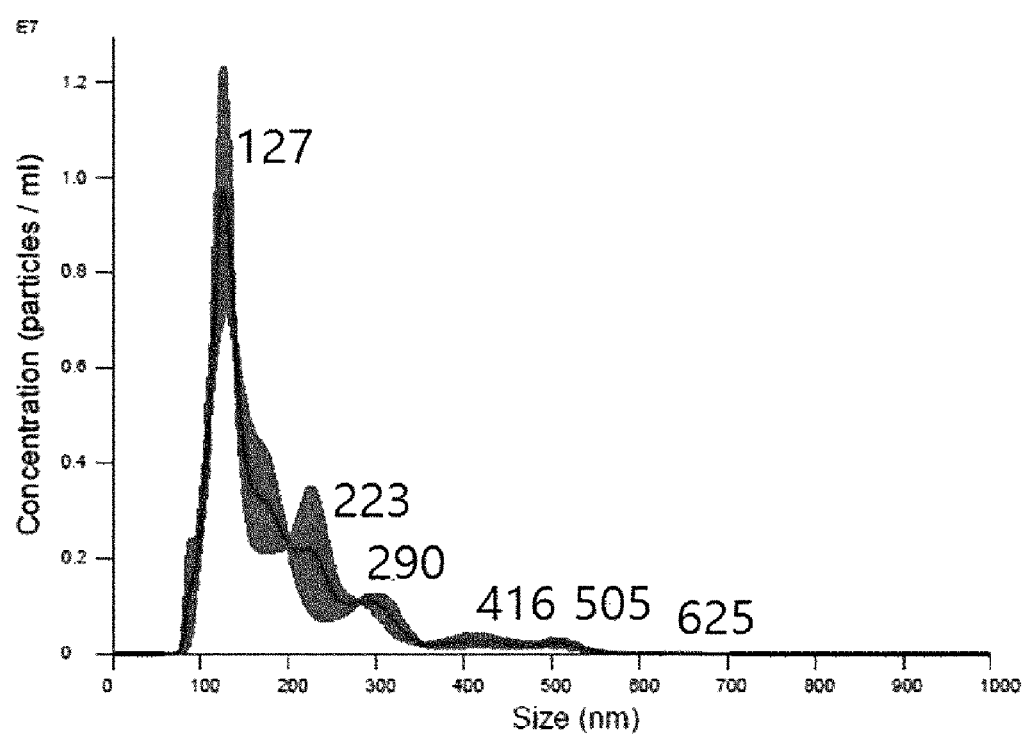

[Fig 8c]
TU17
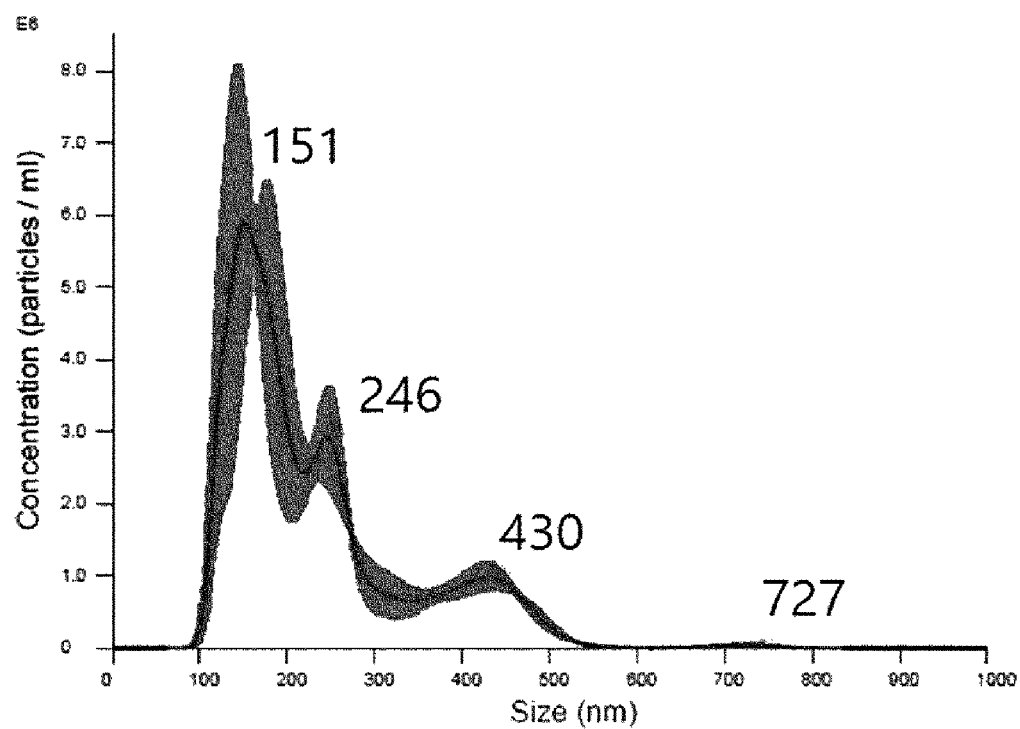

[Fig 8d]
TU114
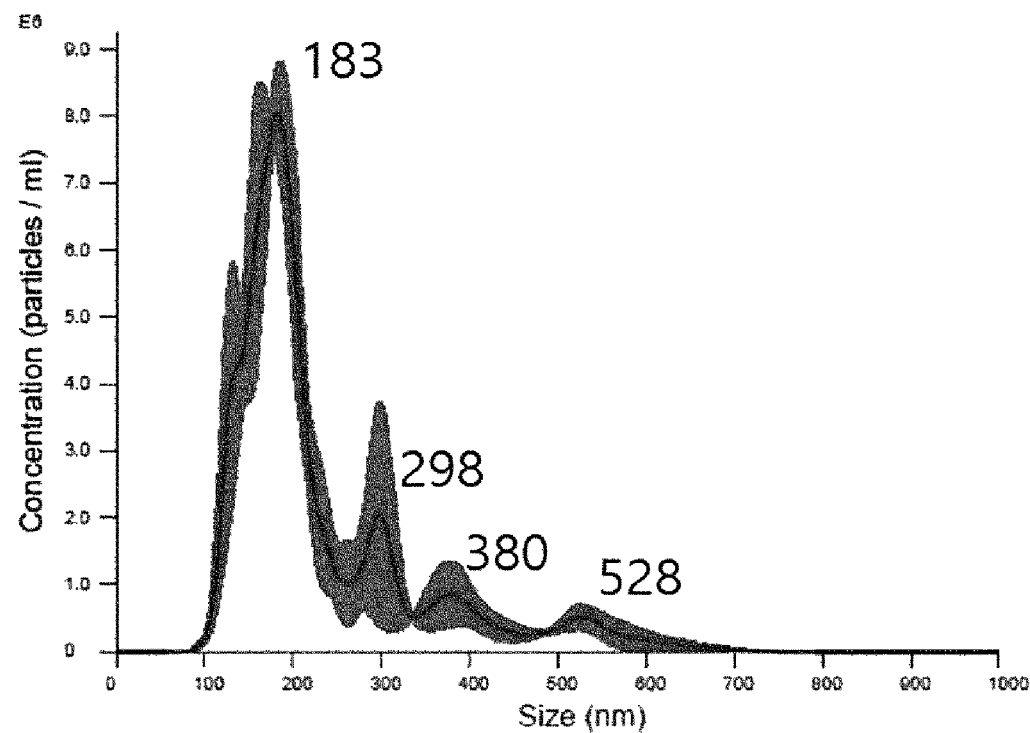
[Fig 9]
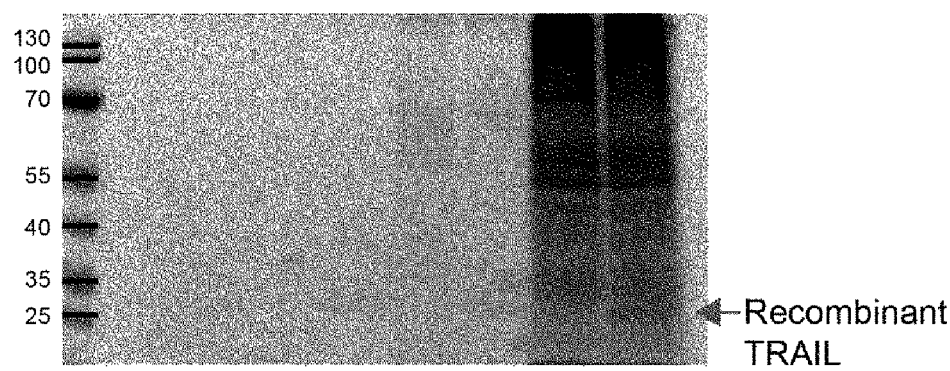

[Fig 10]
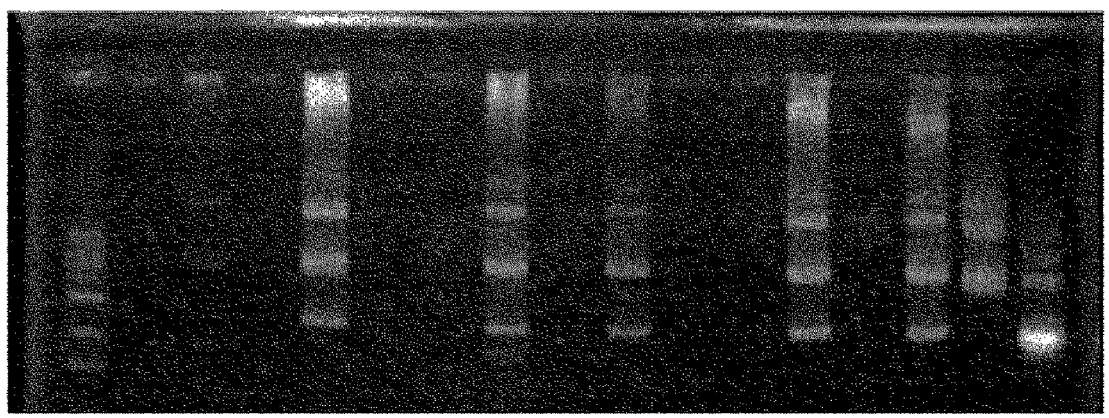
[Fig 11]
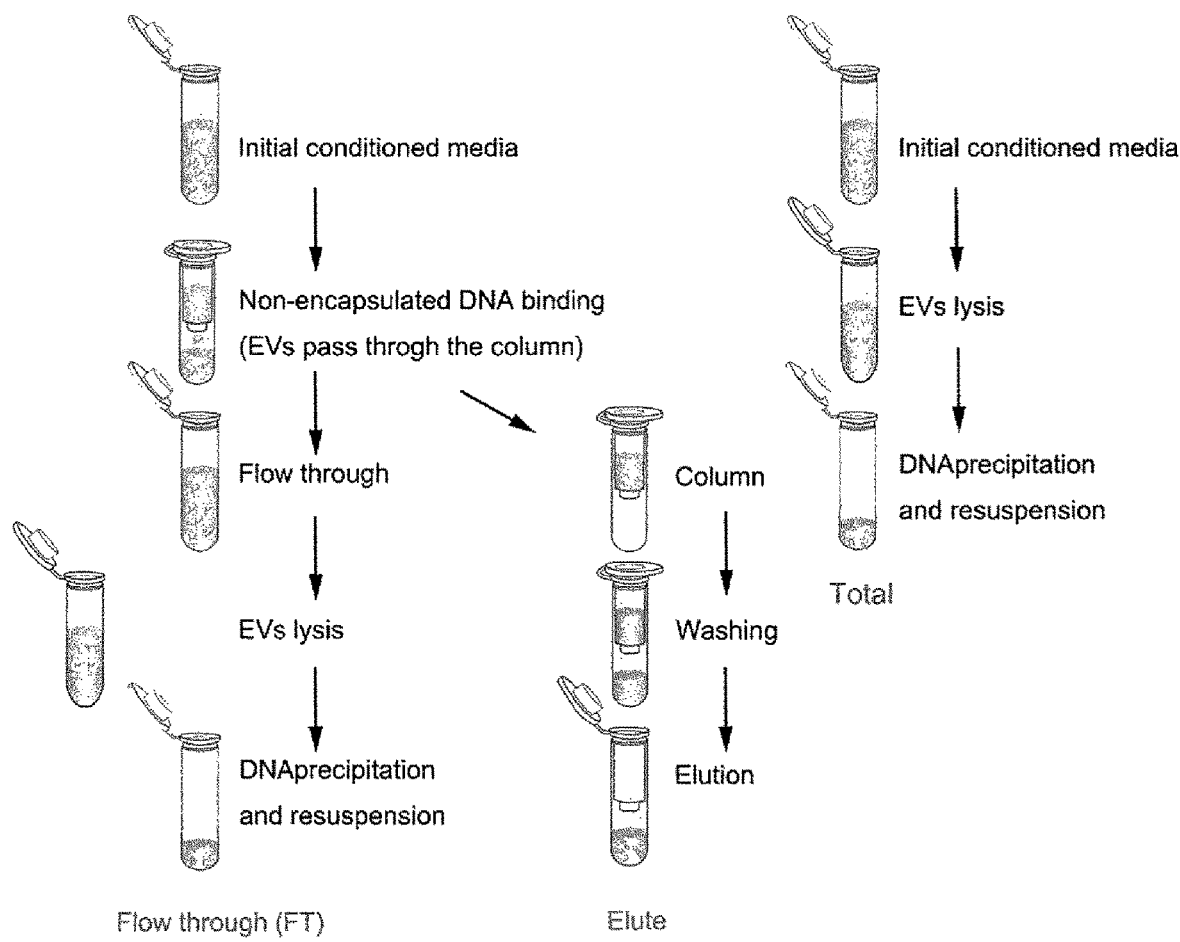

[Fig 12]
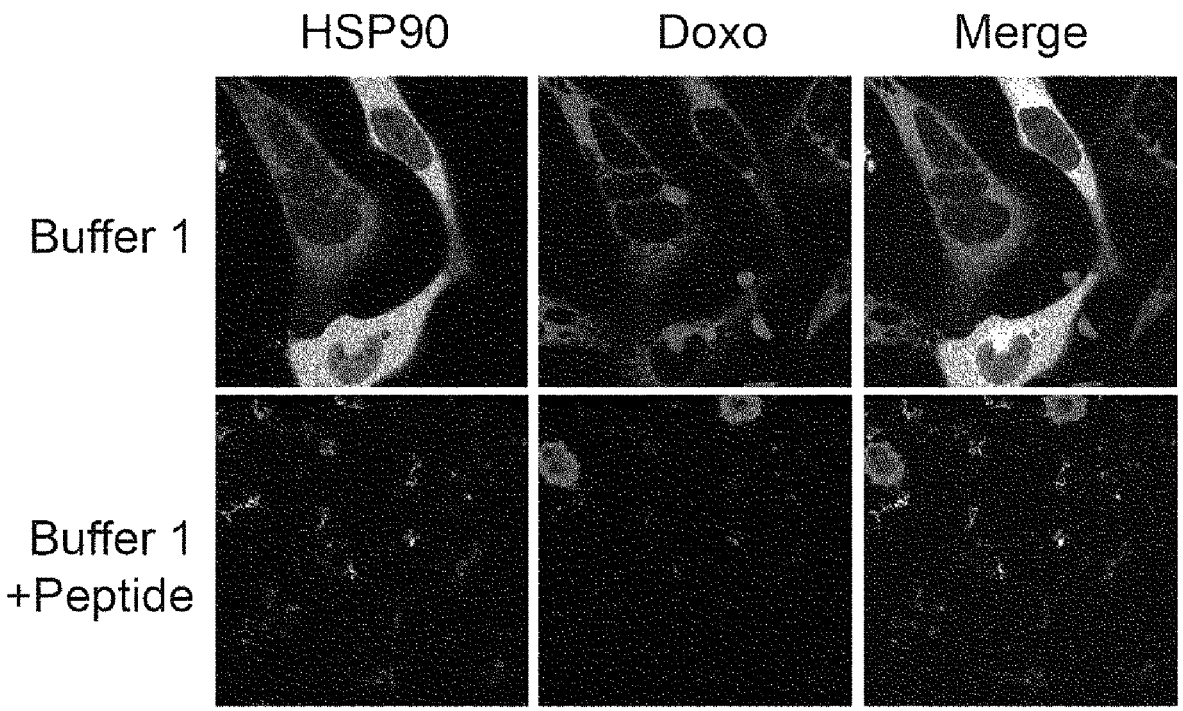
[Fig 13]
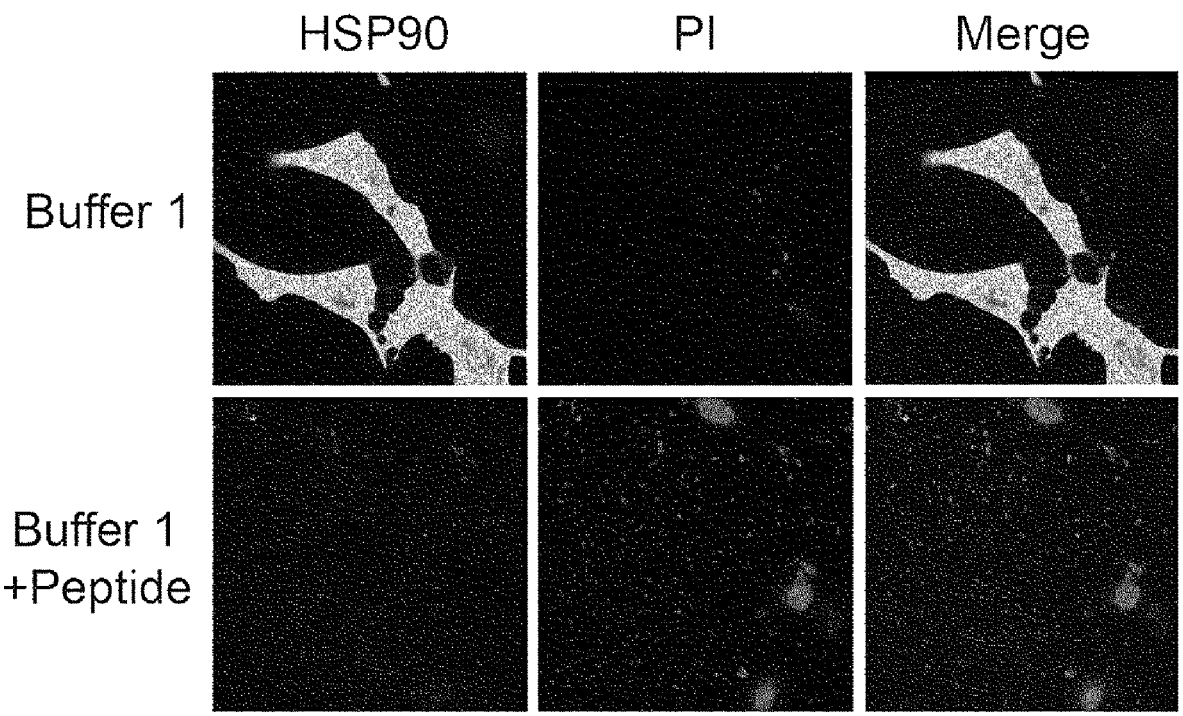

SEQUENCE LISTING

```
<160> NUMBER OF SEQ ID NOS: 21

<210> SEQ ID NO 1
<211> LENGTH: 10
<212> TYPE: PRT
<213> ORGANISM: Artificial Sequence
<220> FEATURE:
<223> OTHER INFORMATION: MTD

<400> SEQUENCE: 1

Lys Leu Leu Asn Leu Ile Ser Lys Leu Phe
1               5                   10

<210> SEQ ID NO 2
<211> LENGTH: 16
<212> TYPE: PRT
<213> ORGANISM: Artificial Sequence
<220> FEATURE:
<223> OTHER INFORMATION: eMTDdelta4

<400> SEQUENCE: 2

Lys Leu Asn Phe Arg Gln Lys Leu Leu Asn Leu Ile Ser Lys Leu Phe
1               5                   10                  15

<210> SEQ ID NO 3
<211> LENGTH: 19
<212> TYPE: PRT
<213> ORGANISM: Artificial Sequence
<220> FEATURE:
<223> OTHER INFORMATION: TU17

<400> SEQUENCE: 3

Arg Pro Ala Arg Pro Ala Arg Gly Gly Lys Leu Leu Asn Leu Ile Ser
1               5                   10                  15

Lys Leu Phe

<210> SEQ ID NO 4
<211> LENGTH: 18
<212> TYPE: PRT
<213> ORGANISM: Artificial Sequence
<220> FEATURE:
<223> OTHER INFORMATION: R(8):MTD

<400> SEQUENCE: 4

Arg Arg Arg Arg Arg Arg Arg Arg Lys Leu Leu Asn Leu Ile Ser Lys
```

-continued

```
1               5                   10                  15

Leu Phe

<210> SEQ ID NO 5
<211> LENGTH: 15
<212> TYPE: PRT
<213> ORGANISM: Artificial Sequence
<220> FEATURE:
<223> OTHER INFORMATION: TU103

<400> SEQUENCE: 5

Lys Leu Leu Asn Leu Trp Ser Leu Leu Phe Gly Tyr Thr Ile Lys
1               5                   10                  15

<210> SEQ ID NO 6
<211> LENGTH: 17
<212> TYPE: PRT
<213> ORGANISM: Artificial Sequence
<220> FEATURE:
<223> OTHER INFORMATION: TU104

<400> SEQUENCE: 6

Met Glu Trp Trp Tyr Leu Leu Lys Leu Leu Asn Leu Ile Ser Lys Leu
1               5                   10                  15

Phe

<210> SEQ ID NO 7
<211> LENGTH: 16
<212> TYPE: PRT
<213> ORGANISM: Artificial Sequence
<220> FEATURE:
<223> OTHER INFORMATION: TU107

<400> SEQUENCE: 7

Leu Arg Ser Leu Arg Asp Lys Leu Leu Asn Leu Ile Ser Lys Leu Phe
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: TU111

<400> SEQUENCE: 8

Gly Leu Lys Ser Leu Arg Lys Leu Leu Asn Leu Ile Ser Lys Leu Phe
1               5                   10                  15

<210> SEQ ID NO 9
<211> LENGTH: 14
<212> TYPE: PRT
<213> ORGANISM: Artificial Sequence
<220> FEATURE:
<223> OTHER INFORMATION: TU114

<400> SEQUENCE: 9

Lys Trp Tyr Ala Lys Leu Leu Asn Leu Ile Ser Lys Leu Phe
1               5                   10

<210> SEQ ID NO 10
<211> LENGTH: 15
<212> TYPE: PRT
<213> ORGANISM: Artificial Sequence
<220> FEATURE:
<223> OTHER INFORMATION: TU124
```

```
<400> SEQUENCE: 10

Lys Leu Leu Asn Leu Trp Ser Leu Leu Lys Gly Tyr Thr Ile Lys
1               5                   10                  15

<210> SEQ ID NO 11
<211> LENGTH: 14
<212> TYPE: PRT
<213> ORGANISM: Artificial Sequence
<220> FEATURE:
<223> OTHER INFORMATION: TU128

<400> SEQUENCE: 11

Ala Glu Tyr Arg Lys Leu Leu Asn Leu Ile Ser Lys Leu Phe
1               5                   10

<210> SEQ ID NO 12
<211> LENGTH: 15
<212> TYPE: PRT
<213> ORGANISM: Artificial Sequence
<220> FEATURE:
<223> OTHER INFORMATION: TU135

<400> SEQUENCE: 12

Ala Glu Tyr Ser Arg Lys Leu Leu Asn Leu Ile Ser Lys Leu Phe
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: TU146

<400> SEQUENCE: 13

Tyr Trp Leu Pro Leu Arg Lys Leu Leu Asn Leu Ile Ser Lys Leu Phe
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: TU149

<400> SEQUENCE: 14

Ala His Phe Leu Arg Lys Leu Leu Asn Leu Ile Ser Lys Leu Phe
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: TU151

<400> SEQUENCE: 15

Ala Phe Phe Leu Arg Lys Leu Leu Asn Leu Ile Ser Lys Leu Phe
1               5                   10                  15

<210> SEQ ID NO 16
<211> LENGTH: 14
<212> TYPE: PRT
<213> ORGANISM: Artificial Sequence
<220> FEATURE:
<223> OTHER INFORMATION: TU155

<400> SEQUENCE: 16
```

```
Gln Phe Ala Gln Tyr Leu Arg Asn Leu Ile Ser Lys Leu Phe
1               5                   10

<210> SEQ ID NO 17
<211> LENGTH: 14
<212> TYPE: PRT
<213> ORGANISM: Artificial Sequence
<220> FEATURE:
<223> OTHER INFORMATION: TU156

<400> SEQUENCE: 17

Lys Val Ser Ile Phe Leu Lys Asn Leu Ile Ser Lys Leu Phe
1               5                   10

<210> SEQ ID NO 18
<211> LENGTH: 16
<212> TYPE: PRT
<213> ORGANISM: Artificial Sequence
<220> FEATURE:
<223> OTHER INFORMATION: TU166

<400> SEQUENCE: 18

Lys Leu Asn Phe Ala Glu Phe Leu Arg Asn Leu Ile Ser Lys Leu Phe
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: TU168

<400> SEQUENCE: 19

Lys Leu Asn Phe Arg Leu Gly Leu Arg Ser Leu Arg Glu Lys Leu Phe
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: TU171

<400> SEQUENCE: 20

Lys Leu Asn Phe Arg Gln Lys Leu Ala Arg Leu Leu Thr Lys Leu Phe
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: TU172

<400> SEQUENCE: 21

Leu Asn Phe Lys Trp Tyr Ser Leu Leu Asn Leu Ile Ser Lys Leu Phe
1               5                   10                  15
```

COMPOSITION FOR PROMOTING EXTRACELLULAR VESICLE PRODUCTION CONTAINING PEPTIDE DERIVED FROM NOXA PROTEIN AND METHOD FOR PRODUCING EXTRACELLULAR VESICLES BY USING SAME

TECHNICAL FIELD

This application claims priority to and the benefit of Korean Patent Application No. 10-2020-0115145 filed in the Korean Intellectual Property Office on 9 Sep. 2020, the disclosure of which is incorporated herein by reference.

The present invention relates to a composition for promoting extracellular vesicle production containing a peptide derived from Noxa protein and to a method for producing extracellular vesicles (EV) by using the same and, specifically, to a composition containing a peptide derived from Noxa protein that plays a key role in apoptosis and to a method for efficiently mass-producing extracellular vesicles by using a solution containing a sugar.

BACKGROUND ART

Extracellular vesicles (EV) are phospholipid bilayer-enclosed vesicles in a unit smaller than the cell and are present in all types of body fluids. Extracellular vesicles serve to exchange contents or information between cells, and have recently been receiving attention due to the potential for being used in a new drug delivery method. Extracellular vesicles have advantages greatly compared with other drug delivery methods in that they receive little resistance from the individual immune systems, are not significantly affected by natural barriers, such as cell membranes, and can have selectivity to specific cells.

Extracellular vesicles are classified into three types: exosomes, apoptotic bodies, and microvesicles (ectosomes) according to the size and generation procedure. Exosomes are 30 to 150 nm in size and are derived from endosomes in cells. Apoptotic bodies are 100 to 5000 nm in size and are derived from the cytoskeleton that is destroyed in the initial stage of apoptosis. Microvesicles are 50 to 1000 nm in size and are formed as the cell membrane protrudes by a specific drug or physical stress. Exosomes and microvesicles among extracellular vesicles are receiving attention as new drug delivery measures, and particularly, many studies are being conducted using exosomes.

Exosomes are made from cell membranes invaginating into cells. When the cell membrane invaginates into the cell through endocytosis, early sorting endosomes (ESE) are formed, and the early sorting endosomes may be combined with the endoplasmic reticulum (ER) or the trans-Golgi network (TGN). Early sorting endosomes form late sorting endosomes (LSE), and then form multivesicular bodies (MVB) containing intraluminal vesicles by bringing other intracytoplasmic substances into endosomes or exporting the substance in the endosomes into the cytoplasm. Multivesicular bodies bind to autophagosomes, and then decompose by combination with lysosomes or expel intraluminal vesicles out of cells by binding to the inside of the cell membrane. The expelled intraluminal vesicles are called exosomes. An indicator for isolating and purifying exosomes includes CD9, CD63, CD81, flotillin, HSP70, HSP90, or the like.

Exosomes perform various functions by moving between cells. Exosomes interact with various organelles in cells, and as a result, exosomes contain not only cellular components, such as proteins, DNA, or RNA, but also amino acids and other metabolites. Therefore, exosomes play a key role in reproduction, development, immune responses, or outbreaks of various diseases including cancer, through interactions between cells.

The use of exosomes for diagnostic and therapeutic purposes is being actively studied. Exosomes can reflect all the substances existing inside and outside cells, and an attempt has been made to diagnose cerebrovascular diseases, central nervous system diseases, and the like by using exosomes and, particularly, exosomes are used to conduct many studies on the diagnosis of cancer. The possibility of cancer diagnosis according to the analysis of DNA, RNA, proteins, or the like contained in exosomes has been recently proposed very frequently.

In addition, exosomes are receiving attention as a new drug delivery means. Exosomes not only enter cells more easily than liposomes, but also receive little resistance from the immune system. Furthermore, abundant ligands present in the membrane surface of exosomes show the possibility of cell-specific delivery through receptors.

Microvesicles are formed as the cell membrane protrudes outward from the cell. Typically, there are microvesicles formed from platelets and red blood cells, and these microvesicles are formed when cells are activated, shear stress is applied, or apoptosis occurs. Microvesicles also have a similar composition to the cell membrane of their origin cell, and thus microvesicles receive little resistance from the immune system, can easily enter the cell, and show the possibility of cell-specific delivery.

However, despite these advantages, it is difficult to efficiently and uniformly mass-produce extracellular vesicles.

DETAILED DESCRIPTION OF THE INVENTION

Technical Problem

In order to solve the above problems, the present inventors completed a method for efficiently and uniformly mass-producing extracellular vesicles (EV) by treating cell lines with a peptide, derived from the Noxa protein that plays a key role in apoptosis, and derivatives thereof under particular conditions.

In addition, the present inventors verified that a substance poorly passing through cell membranes can be loaded in extracellular vesicles.

An aspect of the present invention is to provide a composition for promoting extracellular vesicle production containing a peptide derived from the Noxa protein.

Another aspect of the present invention is to provide a medium for extracellular vesicle production containing: a peptide derived from the Noxa protein; and a solution containing a sugar.

Still another aspect of the present invention is to provide a method for producing extracellular vesicles by using a medium for extracellular vesicle production.

Still another aspect of the present invention is to provide a method for loading an extracellular vesicle payload by using a medium for extracellular vesicle production.

Technical Solution

The present invention is directed to a composition for promoting extracellular vesicle production containing a peptide derived from Noxa protein and a method for producing extracellular vesicles (EV) by using the same and, specifically, to a composition containing a peptide derived from Noxa protein that plays a key role in apoptosis and to a method for efficiently mass-producing extracellular vesicles by using a solution containing a sugar.

Hereinafter, the present disclosure will be described in more detail.

An embodiment of the present invention is directed to a composition for promoting extracellular vesicle production containing a peptide derived from the Noxa protein, a derivative thereof, or a combination thereof.

In the present invention, the Noxa protein binds to Mcl1 and Bcl2A1 via the Bcl-2 homology 3 (BH3) domain to inhibit Mcl1 and Bcl2A1, thereby activating BAX and BAK proteins, and thus Cytochrome-C is released into the cytoplasm to activate the Caspase system, causing apoptosis.

As used herein, the term "peptide" may refer to a linear molecule formed of amino acid residues binding to each other via peptide linkage.

As used herein, the term "derivative" may refer to a peptide having a modification by chemical modification or amino acid addition at the N-terminus, C-terminus, or the like of the peptide of the present invention, but is not limited thereto, and may refer to a peptide, which performs identical or similar functions to the peptide of the present invention.

In an embodiment of the present invention, the peptide derived from the Noxa protein may be a peptide having homology of at least about 60%, at least about 70%, at least about 80%, at least about 90%, at least about 95%, at least about 98%, or at least about 99% to a peptide containing the amino acid sequence of SEQ ID NO: 1.

In another embodiment of the present invention, the peptide derived from the Noxa protein may be a peptide having homology of at least about 60%, at least about 70%, at least about 80%, at least about 90%, at least about 95%, at least about 98%, or at least about 99% to a peptide containing any one amino acid sequence of SEQ ID NOS: 2 to 21.

In the present invention, the peptide may be prepared by a chemical direct synthesis method using solid-phase peptide synthesis, a synthesis method using an automatic synthesizer, or a method of inserting a nucleotide sequence encoding the peptide into a vector and expressing the nucleotide sequence, but is not limited thereto.

As used herein, the term "vector" may refer to a means for expressing a target gene in a host cell.

In the present invention, examples of the vector may include plasmid vectors, cosmid vectors, and viral vectors, such as bacteriophage vector, adenoviral vector, retroviral vector, and adeno-associated viral (AAV) vector, but are not limited thereto.

Another embodiment of the present invention is directed to a medium for extracellular vesicle production, the medium containing at least one peptide selected from the group consisting of peptides containing amino acid sequence of SEQ ID NO: 1 to SEQ ID NO: 21; and a solution containing a sugar.

In the present invention, the concentration of the peptide contained in the solution may be 10 to 80 μM, 10 to 70 μM, 10 to 60 μM, 10 to 50 μM, 10 to 40 μM, 15 to 80 μM, 15 to 70 μM, 15 to 60 μM, 15 to 50 μM, 15 to 40 μM, 20 to 80 μM, 20 to 70 μM, 20 to 60 μM, 20 to 50 μM, or 20 to 40 μM, and for example, 20 to 40 μM, but is not limited thereto.

In the present invention, the sugar may be at least one selected from the group consisting of glucose, sorbitol, and sucrose, and may be for example sucrose, but is not limited thereto.

In the present invention, when the solution contains any sugar other than the glucose of the present invention, the concentration of the glucose contained in the solution may be 3 to 70 mM, 3 to 60 mM, 3 to 50 mM, 4 to 70 mM, 4 to 60 mM, 4 to 50 mM, 5 to 70 mM, 5 to 60 mM, or 5 to 50 mM, and may be for example 5 to 50 mM, but is not limited thereto.

In the present invention, when the solution does not contain any sugar other than the glucose of the present invention, the concentration of glucose contained in the solution may be 80 to 300 mM, 80 to 290 mM, 80 to 280 mM, 80 to 270 mM, 80 to 260 mM, 80 to 250 mM, 90 to 300 mM, 90 to 290 mM, 90 to 280 mM, 90 to 270 mM, 90 to 260 mM, 90 to 250 mM, 100 to 300 mM, 100 to 290 mM, 100 to 280 mM, 100 to 270 mM, 100 to 260 mM, or 100 to 250 mM, and may be for example 100 to 250 mM, but is not limited thereto.

In the present invention, the concentration of sucrose contained in the solution may be 80 to 300 mM, 80 to 290 mM, 80 to 280 mM, 80 to 270 mM, 80 to 260 mM, 80 to 250 mM, 90 to 300 mM, 90 to 290 mM, 90 to 280 mM, 90 to 270 mM, 90 to 260 mM, 90 to 250 mM, 100 to 300 mM, 100 to 290 mM, 100 to 280 mM, 100 to 270 mM, 100 to 260 mM, or 100 to 250 mM, and may be for example 100 to 250 mM, but is not limited thereto.

In the present invention, the concentration of sorbitol contained in the solution may be 100 to 350 mM, 100 to 340 mM, 100 to 330 mM, 100 to 320 mM, 100 to 310 mM, 100 to 300 mM, 125 to 350 mM, 125 to 340 mM, 125 to 330 mM, 125 to 320 mM, 125 to 310 mM, 125 to 300 mM, 150 to 350 mM, 150 to 340 mM, 150 to 330 mM, 150 to 320 mM, 150 to 310 mM, or 150 to 300 mM, and may be for example 150 to 300 mM, but is not limited thereto.

In the present invention, the medium may be at least one selected from the group consisting of a solid-phase medium and a liquid-phase medium, and may be for example a liquid-phase base, but is not limited thereto.

In the present invention, the concentration of 3-(N-morpholino)propanesulfonic acid (MOPS) contained in the solution may be 7 to 13 mM, 7 to 12 mM, 7 to 11 mM, 8 to 13 mM, 8 to 12 mM, 8 to 11 mM, 9 to 13 mM, 9 to 12 mM, 9 to 11 mM, 10 to 13 mM, 10 to 12 mM, 10 to 11 mM, and may be for example 10 mM, but is not limited thereto.

In the present invention, the pH of the solution may be 5 to 10, 5 to 9, 5 to 8, 6 to 10, 6 to 9, 6 to 8, 7 to 10, 7 to 9, or 7 to 8, and may be for example 7 to 8.

In the present invention, the pH of the solution is important in order to produce extracellular vesicles, and extracellular vesicles cannot be produced in a pH of higher than 10 or lower than 5.

In the present invention, the solution may further contain at least one selected from the group consisting of sodium chloride (NaCl), potassium chloride (KCl), sodium gluconate (Na-gluconate), potassium gluconate (K-gluconate), sodium phosphate ($NaPO_4$), and potassium phosphate ($KPO_4$).

In the present invention, the concentration of sodium chloride (NaCl) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In the present invention, the concentration of potassium chloride (KCl) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In the present invention, the concentration of sodium gluconate (Na-gluconate) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In the present invention, the concentration of potassium gluconate (K-gluconate) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In the present invention, the concentration of sodium phosphate (NaPO$_4$) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In the present invention, the concentration of potassium phosphate (KPO$_4$) contained in the solution may be 1 mM or less, and may be 0 to 0.8 mM, 0 to 0.6 mM, 0 to 0.4 mM, 0.1 to 1 mM, 0.1 to 0.8 mM, 0.1 to 0.6 mM, or 0.1 to 0.4 mM, and may be for example 0.1 mM, but is not limited thereto.

In an embodiment of the present invention, the solution may contain 5 mM glucose, 10 mM MOPS, and 250 mM sucrose.

In an embodiment of the present invention, the solution may contain 255 mM glucose and 10 mM MOPS.

In an embodiment of the present invention, the solution may contain 5 mM glucose, 10 mM MOPS, and 250 mM sorbitol.

Still another embodiment of the present invention is directed to a method for producing extracellular vesicles, the method including the following steps:
  a medium preparing step of preparing a medium containing: at least one peptide selected from the group consisting of peptides containing amino acid sequence of SEQ ID NO: 1 to SEQ ID NO: 21; and a solution containing a sugar; and
  a mixing step of mixing the medium and a cell line.

In the present invention, the cell line may be one selected from the group consisting of mouse colon carcinoma (CT26), human cervical cancer (HeLa), human renal epithelium (HEK293), mouse adipocytes (3T3-L1), and human mesenchymal stem cells (HMSC), and may be for example HeLa or HEK293, but is not limited thereto.

Still another embodiment of the present invention is directed to a method for loading an extracellular vesicle payload, the method including:
  a medium preparing step of preparing a medium containing: at least one peptide selected from the group consisting of peptides containing amino acid sequence of SEQ ID NO: 1 to SEQ ID NO: 21; and a solution containing a sugar; and
  a mixing step of mixing the medium, a payload, and a cell line.

In the present invention, the payload may be at least one selected from the group consisting of proteins, DNA, RNA, plasmid DNA, and an anticancer substance, and may be for example plasmid DNA, but is not limited thereto.

In the present invention, the loading may refer to loading the payload in the extracellular vesicles, but is not limited thereto.

In the present invention, the anticancer substance may be at least one selected from the group consisting of an anticancer protein, a tumor suppressing gene, and an anticancer compound, but is not limited thereto.

In the present invention, the anticancer protein may be at least one selected from the group consisting of asparaginase, Botulinum toxin, Tetanus toxin, Shiga toxin, Diphtheria toxin (DT), ricin, Pseudomonas exotoxin (PE), cytolysin A (ClyA), y-Gelonin, Vascular endothelial growth factor (VEGF), angiopoietin 1 (Ang1), angiopoietin 2 (Ang2), transforming growth factor-β, TGF-βintegrin, vascular endothelial (VE)-cadherin, plasminogen activator (PA), ephrin, platelet-derived growth factor (PDGF), monocyte chemotactic protein-1 (MCP-1), fibroblast growth factor (FGF), placenta growth factor (PlGF), von HippelLindau (VHL), adenomatous polyposis coli (APC), cluster of differentiation 95 (CD95), suppression of tumorigenicity 5 (ST5), Yippee like 3 (YPEL3), suppression of tumorigenicity 7 (ST7), and suppression of tumorigenicity 14 (ST14), but is not limited thereto.

In the present invention, the tumor suppressing gene may be at least one selected from the group consisting of von HippelLindau (VHS), adenomatous polyposis coli (APC), cluster of differentiation 95 (CD95), suppression of tumorigenicity 5 (ST5), yippee like 3 (YPEL3), suppression of tumorigenicity 7 (ST7), and suppression of tumorigenicity 14 (ST14), but is not limited thereto.

In the present invention, the anticancer compound may be at least one selected from the group consisting of methotrexate, 5-fluorouracil, gemcitabine, arabinosylcytosine, hydroxy urea, mercaptopurine, thioguanine, nitrogen Mustard, cyclosporamide, anthracycline, daunorubicin, doxorubicin, epirubicin, idarubicin, pixantrone, sabarubicin, valrubicin, actinomycin D, vincristine, Taxol, combretastatin A4, Fumagillin, herbimycin A, 2-methoxyestradiol, OGT 2115, TNP 470, tranilast, XRP44X, thalidomide, endostatin, salmosin, angiostatin, plasminogen, a kringle domain of apolipoprotein, oxalopatin, carboplatin, cisplatin, bortezomib, and radionuclides, but is not limited thereto.

Advantageous Effects

The use of the peptide for promoting extracellular vesicle production and the method for producing extracellular vesicles by using the same of the present invention can efficiently and uniformly mass-produce extracellular vesicles, and can efficiently produce extracellular vesicles which load drugs poorly passing through cellular membranes as well as recombinant proteins or plasmid DNA

BRIEF DESCRIPTION OF THE DRAWINGS

FIG. 1 shows microscopic observation images of extracellular vesicles generated and settled on the bottom of the plate when the HeLa cell line was treated with the eMTDΔ4 peptide in combination with a solution according to an example of the present invention.

FIG. 2 shows microscopic observation images of extracellular vesicles generated when the HeLa cell line was treated with the eMTDΔ4 peptide in combination with solutions according to examples of the present invention.

FIG. 3 shows microscopic observation images of extracellular vesicles generated when the HeLa cell line was treated with the eMTDΔ4 peptide in combination with a solution containing glucose, sorbitol, or sucrose.

FIG. 4 shows confocal microscopic observation images of extracellular vesicles formed after the transfection of the HeLa cell line with HSP90, an exosome indicator, with EGFP, a fluorescent protein, attached thereto.

FIG. 5 shows images, taken by using a confocal microscope every two seconds, of the generation of extracellular vesicles after the membrane proteins CD9 and CD81 to which mEmerald and mCherry were attached, respectively, were transfected into HeLa cell lines.

FIG. 6 shows images depicting the sizes of extracellular vesicles generated in the HeLa cell line, as measured by an atomic microscope.

FIG. 7 shows heat-maps depicting the quantities of extracellular vesicles produced by MTD, and eMTDΔ4 and derivatives thereof in the HEK-293 cell line, as quantified by Bradford solution.

FIG. 8 shows graphs depicting the sizes and quantities of extracellular vesicles produced by MTD, and eMTDΔ4 and derivatives thereof in the HEK-293 cell line, as analyzed by the Nanoparticle Tracking Analysis (NTA) system.

FIG. 9 shows the results of performing acrylamide gel electrophoresis after the TRAIL protein, which is a recombinant protein, was loaded in extracellular vesicles.

FIG. 10 shows the results of performing agarose gel electrophoresis after pUC19 and pEGFP-C1, which are plasmid DNA, were loaded in extracellular vesicles.

FIG. 11 is a schematic diagram of a procedure where plasmid DNA was loaded in extracellular vesicles and isolated therefrom.

FIG. 12 shows images confirming the results by a confocal microscope after doxorubicin, a drug favorably passing through cell membranes, was loaded in extracellular vesicles produced by the treatment of the HeLa cell line with eMTDΔ4.

FIG. 13 shows images confirming the results by a confocal microscope after propidium iodide (PI), a drug poorly passing through cell membranes, was loaded in extracellular vesicles produced by the treatment of the HeLa cell line with eMTDΔ4.

MODE FOR CARRYING OUT THE INVENTION

Hereinafter, the present invention will be described in more detail with reference to exemplary embodiments. These exemplary embodiments are provided only for the purpose of illustrating the present disclosure in more detail, and therefore, according to the purpose of the present disclosure, it would be apparent to a person skilled in the art that these examples are not construed to limit the scope of the present disclosure.

Preparative Example 1: Preparation of Noxa Protein-Derived Peptide and Derivatives Thereof The mitochondrial targeting domain (MTD) of Noxa protein is shown as SEQ ID NO: 1 on Table 1. For the synthesis of a peptide derived from MTD, a manual Fmoc synthesis method in units of 0.25 mmol was basically used. Specifically, a resin was cleanly washed with dimethylformamide (DMF), and then 10 mL of a 20% piperidine/DMF solution was added to the resin. After stirring for 1 minute, 10 mL of a 20% piperidine/dimethylformamide solution was again added thereto and shaken for 30 minutes. After the resin was again washed with dimethylformamide, no piperidine remained was confirmed through the ninhydrin test (resin turned blue).

The following solutions were prepared for coupling: 1 mmol Fmoc-amino acid, 2.1 ml of 0.45 M 2-(1H-benzotriazol-1-yl)-1,1,3,3-tetramethyluronium hexafluorophosphate, hexafluorophosphate Benzotriazole Tetramethyl Uronium/Hydroxybenzotriazole (HBTU/HOBT, 1 mmol), 348 μL of N,N-diisopropylethylamine (DIEA, 2 mmol).

The prepared solution was added to the resin, and shaken for 30 minutes. After the solution was drained from the resin, the resin was washed with dimethyl formamide. Then, for coupling of amino acids, the solution was again added, and then a coupling step was repeated to synthesize Noxa protein-derived eMTDΔ4 and derivative peptides thereof.

The peptides thus synthesized were analyzed by high-performance liquid chromatography, Instrument: Waters 2690 separations module, Flow rate: 1.0 ml/min, gradient: 0-20% B, 5 minutes; 20-50%, B 20 minutes; 50-80%, B 5 minutes, A; 0.1% TFA water, B; 0.1% TFA acetonitrile, column: waters C18, 5 microns, Detection: 220 nm, purity: 95%) and a mass analyzer (HP 1100 series LC/MSD). The synthesized peptides are shown as SEQ ID NO: 2 to SEQ ID NO: 21 on Table 1.

TABLE 1

| SEQ ID NO | Name | Sequence | Note |
|---|---|---|---|
| 1 | MTD | KLLNLISKLF | 10aa |
| 2 | eMTDΔ4 | KLNFRQKLLNLISKLF | 16aa |
| 3 | TU17 | RPARPARGGKLLNLISKLF | 19aa |
| 4 | R(8):MTD | RRRRRRRRKLLNLISKLF | 18aa |
| 5 | TU103 | KLLNLWSLLFGYTIK | 15aa |
| 6 | TU104 | MEWWYLLKLLNLISKLF | 17aa |
| 7 | TU107 | LRSLRDKLLNLISKLF | 16aa |
| 8 | TU111 | GLKSLRKLLNLISKLF | 16aa |
| 9 | TU114 | KWYAKLLNLISKLF | 14aa |
| 10 | TU124 | KLLNLWSLLKGYTIK | 15aa |
| 11 | TU128 | AEYRKLLNLISKLF | 14aa |
| 12 | TU135 | AEYSRKLLNLISKLF | 15aa |
| 13 | TU146 | YWLPLRKLLNLISKLF | 16aa |
| 14 | TU149 | AHFLRKLLNLISKLF | 15aa |
| 15 | TU151 | AFFLRKLLNLISKLF | 15aa |
| 16 | TU155 | QFAQYLRNLISKLF | 14aa |
| 17 | TU156 | KVSIFLKNLISKLF | 14aa |
| 18 | TU166 | KLNFAEFLRNLISKLF | 16aa |
| 19 | TU168 | KLNFRLGLRSLREKLF | 16aa |
| 20 | TU171 | KLNFRQKLARLLTKLF | 16aa |
| 21 | TU172 | LNFKWYSLLNLISKLF | 16aa |

Example 2: Preparation of Solutions for Extracellular Vesicle Production

For extracellular vesicle production using eMTDΔ4, derived from the mitochondrial targeting domain of Noxa protein, and the derivative peptides thereof, the solutions of Example 1 and Comparative Examples 1 to 18 containing the compositions and contents shown in Table 2 were prepared.

TABLE 2

| (mM) | Glucose | MOPS | NaCl | KCl | Na-gluconate | K-gluconate | Sucrose | NaPO$_4$ (pH7.4) | KPO$_4$ (pH7.4) |
|---|---|---|---|---|---|---|---|---|---|
| Example 1 | 5 | 10 | — | — | — | — | 250.00 | — | — |
| Comparative Example 1 | 5 | 10 | 145 | — | — | — | — | — | — |
| Comparative Example 2 | 5 | 10 | — | 145 | — | — | — | — | — |
| Comparative Example 3 | 5 | 10 | — | — | 145 | — | — | — | — |
| Comparative Example 4 | 5 | 10 | — | — | — | 145 | — | — | — |
| Comparative Example 5 | 5 | 10 | 50 | — | 95 | — | — | — | — |
| Comparative Example 6 | 5 | 10 | — | 50 | — | 95 | — | — | — |
| Comparative Example 7 | 5 | 10 | — | — | — | — | 241.37 | 10 | — |
| Comparative Example 8 | 5 | 10 | — | — | — | — | 232.37 | 20 | — |
| Comparative Example 9 | 5 | 10 | — | — | — | — | 200.00 | 58 | — |
| Comparative Example 10 | 5 | 10 | 75 | — | — | — | 91.37 | 10 | — |
| Comparative Example 11 | 5 | 10 | 75 | — | — | — | 82.75 | 20 | — |
| Comparative Example 12 | 5 | 10 | 75 | — | — | — | 50.00 | 58 | — |
| Comparative Example 13 | 5 | 10 | — | — | — | — | 241.37 | — | 10 |
| Comparative Example 14 | 5 | 10 | — | — | — | — | 232.37 | — | 20 |
| Comparative Example 15 | 5 | 10 | — | — | — | — | 200.00 | — | 58 |
| Comparative Example 16 | 5 | 10 | — | 75 | — | — | 91.37 | — | 10 |
| Comparative Example 17 | 5 | 10 | — | 75 | — | — | 82.75 | — | 20 |
| Comparative Example 18 | 5 | 10 | — | 75 | — | — | 50.00 | — | 58 |

Experimental Example 1: Culture of Cancer Cell Lines 1-1. Preparation of Cell Lines and Reagents Cancer cell lines were cultured prior to testing the activity to induce extracellular vesicle production by the Noxa protein-derived peptide and the derivatives thereof in Preparative Example 1.

Dulbecco's modified eagle medium (DMEM), RPMI 1640, fatal bovine serum (FBS), trypsin-ethylenediaminetetraacetic acid (trypsin-EDTA), and Hank's balanced salt solution (HBSS) required for culture were purchased from Gibco, and Effectene, which is a transfection reagent, was purchased from Qiagen. HeLa and HEK293 cell lines were purchased from Korean Cell Line Bank (KCLB).

1-2. Cell Culture

HeLa and HEK293 cell lines were subcultured at least three times before use in experiments. The HeLa cell line was cultured using DMEM containing 10% fetal bovine serum (FBS) and the HEK-293 cell line was cultured using RPMI 1640 containing 10% fetal bovine serum, under a gas condition of 5% (v/v) CO$_2$ and a temperature condition of 37° C.

Experimental Example 2: Production of Extracellular Vesicles 2-1. Production of Extracellular Vesicles After the HeLa cell line was cultured in a 6-well plate, the culture was removed, and then the HeLa cell line was treated with the solution in Example 1.

The control group was not treated with any peptide, and the experiment group was treated with eMTDΔ4 peptide of SEQ ID NO: 2 (final concentration: 20 μM). After 10 minutes, the generation of extracellular vesicles was observed by an optical microscope (bright field), and the observation results are shown in FIG. 1.

As can be confirmed in FIG. 1, the bottom of the plate was clean in the control group, but small extracellular vesicle particles were formed and settled on the bottom of the plate in the experiment group.

2-2. Production of Extracellular Vesicles Using Various Solutions

Extracellular vesicle production was carried out by the experimental method of Experimental Example 2-1 using the R(8):MTD peptide of SEQ ID NO: 4 and the solutions of Example 1 and Comparative Examples 1 to 18, and the results are shown in FIGS. 2A to 2S.

As can be confirmed in FIG. 2A, many extracellular vesicle particles were generated and most of the particles were settled on the bottom of the plate.

However, as can be confirmed in FIGS. 2B to 2S, extracellular vesicle particles were not generated, and thus no extracellular vesicles settled on the bottom of the plate could be observed, and only the formation of particles that occurs at the time of apoptosis inside cells was observed.

2-3. Production of Extracellular Vesicles Using Various Sugars

Extracellular vesicle production was carried out by the experimental method of Example 2-1 using the R(8):MTD peptide of SEQ ID NO: 4 and the solutions of Examples 1 to 3 on Table 3, and the results are shown in FIGS. 3A to 3C.

TABLE 3

| (mM)      | Glucose | Sucrose | Sorbitol | MOPS |
|-----------|---------|---------|----------|------|
| Example 1 | 5       | 250     | —        | 10   |
| Example 2 | 255     | —       | —        | 10   |
| Example 3 | 5       | —       | 250      | 10   |

As can be confirmed in FIGS. 3A to 3C, even when an excess of glucose or sorbitol, instead of sucrose, was added to the solution, extracellular vesicles were well formed.

Experimental Example 3: Identification of Extracellular Vesicle Morphology

In order to transfect the HSP90 protein, an exosome indicator, into the HeLa cell line, the HeLa cell line was cultured overnight in a 6-well plate, and then treated with a plasmid into which Effectene and pEGFP-HSP90 were cloned, and after 4 hours, the culture was replaced.

The next day, the culture was removed from the HeLa cell line, and the solution of Example 1 was added. A control group was not treated with any peptide, and an experiment group was treated with the eMTDΔ4 peptide of SEQ ID NO: 2 (final concentration: 20 μM). The HSP90 protein was excited using an argon laser of 488 nm. After 10 minutes, the control group and the experiment group were observed using a confocal microscope (Leica TCS SP5 Microsystems), and the results are shown in FIG. 4.

As can be confirmed in FIG. 4, the cell morphology of the control group was not damaged and the HSP90 protein was located in the cytoplasm. However, in the experiment group (eMTDΔ4), the cell morphology was damaged and extracellular vesicles containing the HSP90 protein were settled on the bottom of the plate.

The reasoning was determined to be that the HSP90 protein of the cytoplasm was released out of the cell through the cell membrane defects that occurred during the production of extracellular vesicles.

Experimental Example 4: Investigation of Production of Extracellular Vesicles

The HeLa cell line was cultured in a 12-well plate overnight, and in order to identify the CD9 protein, an extracellular vesicle indicator, the HeLa cell line was treated with a plasmid into which Effectene and mEmerald-CD9 were cloned, and after 4 hours, the culture was replaced.

The next day, the culture was removed from the HeLa cell line, and the HeLa cell line was treated with the solution of Example 1. After each HeLa cell line was treated with the eMTDΔ4 peptide (final concentration: 20 μM), a laser having a wavelength of 488 nm was used to excite mEmerald-CD9. Thereafter, the cells were observed for 10 minutes while images were taken every 2 seconds by using a confocal microscope, and the results are shown in FIG. 5A.

In order to identify the CD81 protein, an extracellular vesicle indicator, the same procedure as in the method for observing the CD9 protein was performed except that the HeLa cells were treated with a plasmid into which mCherry-CD81 instead of mEmerald-CD9 was cloned and mCherry-CD81 was excited using a laser having a wavelength of 561 nm, and the results are shown in FIG. 5B.

As can be confirmed in FIGS. 5A and 5B, both CD9 and CD81 proteins were sufficient to observe the formation of extracellular vesicles, and CD9 and CD81 proteins were released into the extracellular matrix. It could be verified that extracellular vesicles were released to the extracellular matrix within a few seconds after generation, although the release procedure could not be specifically identified.

Experimental Example 5: Identification of Extracellular Vesicle Size

The HeLa cell line was cultured in a culture plate, treated with the eMTDΔ4 peptide (final concentration: 20 μM) in combination with the solution of Example 1 and, after 10 minutes, fixed with 4% (v/v) paraformaldehyde.

Thereafter, the cells were observed using an atomic microscope (Surface Imaging Systems, NANO Station II, with a cantilever with a pyramidal-shaped tip, a frequency of 146-236 kHz, a spring constant of 21-98 N/m, a length of 225 nm, and a resistance of 0.01-0.02 Ωcm), and the observation results are shown in FIGS. 6A to 6C.

As can be confirmed in FIG. 6A, extracellular vesicles with various sizes were generated, and the sizes thereof could be measured. The results of measuring the sizes of extracellular vesicles are shown as graphs in FIGS. 6B and 6C.

As can be confirmed in FIGS. 6B and 6C, the sizes of extracellular vesicles were measured to be about 200 nm. These results prove that the extracellular vesicles of the present invention have a size similar to the previously known extracellular vesicle sizes.

Experimental Example 6: Verification of Extracellular Vesicle Output

The 293-HEK cell line was cultured in a 6-well plate at a rate of $2 \times 10^5$ cells/mL, and the next day, the cell line was treated with the solution of Example 1 and a peptide of any one of SEQ ID NOs: 1 to 21. After minutes, the solution was removed, followed by centrifugation at an RCF of 12000, and the extracellular vesicles were quantified using the supernatant by Bradford solution. The results are shown in FIG. 7 and Table 4.

TABLE 4

| | | Amount of proteins contained in extracellular vesicles (unit: μg/μl) | | |
|------|-------------------|-------|-------|-------|
| Item | Name              | 10 μM | 20 μM | 40 μM |
| 1    | Media (Control)   | 1.03  | 0.75  | 0.76  |
| 2    | MTD               | 0.80  | 1.17  | 2.87  |
| 3    | eMTDΔ4            | 4.93  | 6.40  | 7.56  |
| 4    | TU103             | 0.75  | 0.40  | 0.55  |
| 5    | TU104             | 0.62  | 0.75  | 1.02  |
| 6    | TU107             | 5.58  | 6.69  | 7.45  |
| 7    | TU111             | 4.17  | 4.98  | 6.44  |
| 8    | TU124             | 3.30  | 5.02  | 6.24  |
| 9    | TU128             | 3.86  | 5.29  | 7.25  |
| 10   | TU135             | 1.81  | 4.41  | 6.54  |
| 11   | TU146             | 2.01  | 2.89  | 3.50  |
| 12   | TU149             | 1.71  | 2.00  | 2.57  |
| 13   | TU151             | 1.51  | 1.30  | 1.40  |
| 14   | TU155             | 1.56  | 1.77  | 2.85  |
| 15   | TU156             | 1.17  | 1.55  | 3.93  |
| 16   | TU166             | 5.77  | 6.68  | 8.10  |
| 17   | TU168             | 0.77  | 2.17  | 3.74  |
| 18   | TU171             | 2.64  | 3.62  | 5.30  |
| 19   | TU172             | 0.83  | 0.44  | 0.59  |

As can be confirmed in FIG. 7 and Table 4, most of the peptides shown in Table 4 well produced extracellular vesicles although there is a difference in output.

In addition, as the final peptide treatment concentration increased from 10 µM to 20 µM and 40 µM, the amount of proteins contained in the extracellular vesicles tended to increase.

Experimental Example 6: Identification of Extracellular Vesicle Size and Quantity After the 293-HEK cell line was cultured to 90% confluency (about 2×10$^7$ cells) in a 10-cm culture dish, the culture was removed, and the cells were treated with the eMTDΔ4 peptide (final concentration: 20 µm), which has been dissolved in 5 ml of the solution of Example 1. After 20 minutes, the solution was removed, followed by centrifugation at an RCF of 12000, and then the size and quantity of extracellular vesicles were measured using a Nanoparticle Tracking Analysis (NTA) system (Nanosight LM10, Malvern Instruments). The results are shown in FIGS. 8A to 8D and Table 5.

TABLE 5

| | Stats: | Merged data (nm) | Quantity (/ml, 50-fold diluted) |
|---|---|---|---|
| eMTDΔ4 | Mean | 184.5 | 7.44 × 10$^8$ ± 6.51 × 10$^7$ |
| | Mode | 126.3 | |
| | SD | 87.8 | |
| | D10 | 111.0 | |
| | D50 | 152.6 | |
| | D90 | 298.4 | |
| MTD | Mean | 181.1 | 8.01 × 10$^8$ ± 1.75 × 10$^7$ |
| | Mode | 115.6 | |
| | SD | 75.2 | |
| | D10 | 113.4 | |
| | D50 | 154.9 | |
| | D90 | 288.5 | |
| TU17 | Mean | 229.6 | 7.95 × 10$^8$ ± 7.15 × 10$^7$ |
| | Mode | 150.9 | |
| | SD | 104.3 | |
| | D10 | 131.6 | |
| | D50 | 193.2 | |
| | D90 | 407.9 | |
| TU114 | Mean | 231.1 | 8.75 × 10$^8$ ± 9.27 × 10$^7$ |
| | Mode | 182.3 | |
| | SD | 110.2 | |
| | D10 | 137.9 | |
| | D50 | 191.3 | |
| | D90 | 390.5 | |

As can be confirmed in FIGS. 8A to 8D and Table 5, with respect to the size of extracellular vesicles, the mean was 184.5 nm, the mode was 126.3 nm, and the standard deviation (SD) was 87.8 nm when the eMTDΔ peptide was used.

The mean was 181.1 nm, the mode was 115.6 nm, and the standard deviation was 75.2 nm when the MTD peptide was used.

The mean was 229.6 nm, the mode was 150.9 nm, and the standard deviation was 104.3 nm when the TU17 peptide was used.

The mean was 231.1 nm, the mode was 182.3 nm, and the standard deviation was 110.2 nm when the TU114 peptide was used.

It could be therefore verified that when the peptide for promoting extracellular vesicle production of the present invention is used under a specific solution condition, extracellular vesicles with various sizes can be efficiently mass-produced.

Experimental Example 7: Production of Extracellular Vesicles Loading Recombinant Protein After the 293-HEK cell line was cultured to 90% confluency in a 6-well plate, the culture was removed, and the cell line was treated with the eMTDΔ4 peptide (final concentration: 25 µM) and the recombinant TRAIL, which have been dissolved to concentrations of 25 µM and 2 µg/ml in the solution of Example 1, respectively. The supernatant was collected, and PEG (final concentration: 8%) was added, followed by centrifugation at an RCF of 12000 for 10 minutes, thereby settling extracellular vesicles, and the extracellular vesicles were loaded on the SDS-acrylamide gel to check the TRAIL protein. The results are shown in FIG. 9 and Table 6.

TABLE 6

| | Treated or not | | | | | | | |
|---|---|---|---|---|---|---|---|---|
| Cell | − | − | − | − | + | + | + | + |
| Recombinant TRAIL | − | + | − | + | − | + | − | + |
| Peptide | − | − | + | + | − | − | + | + |
| Protein detected or not | X | X | X | X | X | X | X | ○ |

As can be confirmed from FIG. 9 and Table 6, when the peptide for promoting extracellular vesicle production of the present invention was used under a specific solution condition, a recombinant protein externally added during the production of extracellular vesicles can be efficiently loaded in the extracellular vesicles.

Experimental Example 8: Production of Extracellular Vesicles Loading Plasmid DNA After the 293-HEK cell line was cultured to 90% confluency in a 6-well plate, the culture was removed, and the cell line was treated with the eMTDΔ4 peptide (final concentration: 25 µM) and plasmid DNA (PUC19 3 µg/ml, EGFP-C1 6 µg/ml), which have been dissolved in the solution of Example 1.

1.15 ml of the supernatant was collected and 0.35 ml of Qiagen buffer P3 was added, thereby making a total volume of 1.5 ml, of which 0.75 ml was then passed through the DNA miniprep column (Qiagen), and the passed solution was purified with phenol and precipitated with ethanol.

After 30 µl of DNA bound to the column and 30 µl of DNA precipitated with ethanol were dissolved in water, 10 µl of DNA bound to the column and 10 µl of DNA precipitated with ethanol were subjected to agarose gel electrophoresis, and then stained with EtBr. The results are shown in FIG. 10.

As can be confirmed in FIG. 10, the plasmid DNA externally added during the production of extracellular vesicles can be loaded in the extracellular vesicles.

In addition, the plasmid DNA could be again isolated from the extracellular vesicles by the process shown in FIG. 11.

Therefore, when the peptide for promoting extracellular vesicle production of the present invention is used under a specific solution condition, plasmid DNA can be efficiently loaded in extracellular vesicles.

Experimental Example 9: Production of Extracellular Vesicles Loading Doxorubicin Doxorubicin, which is a drug passing through cell membranes well, is used to treat cancers, such as breast cancer, bladder cancer, Kaposi's sarcoma, lymphoma, or acute lymphoblastic leukemia. First, the HeLa cell line was cultured in a 12-well plate overnight, then transfected with a plasmid expressing EGFP-HSP90 using effectene, and then the culture was replaced after 4 hours. The next day, the culture was removed from the HeLa cell line to prepare a cell line.

The control group was treated with only doxorubicin without any peptide, and the experiment group was treated with the eMTDΔ4 peptide (final concentration: 25 μM) and doxorubicin (final concentration: 100 μM), which have been dissolved in the solution of Example 1, and then after 10 minutes, the groups were observed by a confocal microscope. The results are shown in FIG. 12.

As can be confirmed in FIG. 12, the generated extracellular vesicles contained doxorubicin as well as the HSP90 protein, an exosome indicator.

Experimental Example 10: Production of Extracellular Vesicles Loading Propidium Iodide (PI)

Propidium iodide (PI), which is a drug poorly passing through cell membranes, is a fluorescent substance capable of being used to stain cells. First, the HSP90 protein was transfected into the HeLa cell line to prepare a cell line.

The control group was treated with only PI without any peptide, and the experiment group was treated with the eMTDΔ4 peptide (final concentration: 25 μM) and 5 μg/ml PI, which have been in combination dissolved in the solution of Example 1, and then after 10 minutes, the groups were observed by a confocal microscope. The results are shown in FIG. 13.

As can be confirmed in FIG. 13, the generated extracellular vesicles contained PI as well as the HSP90 protein, an exosome indicator.

Therefore, proteins, DNA, various drugs that cannot pass through cell membranes, and the like can be loaded in the extracellular vesicles, which would be advantageously used as a new drug delivery system.

The invention claimed is:

1. A medium for extracellular vesicle production, the medium comprising: at least one peptide selected from the group consisting of SEQ ID NOs: 2 and 5-15; and a solution containing a sugar.

2. The medium of claim 1, wherein the sugar is at least one selected from the group consisting of glucose, sucrose, and sorbitol.

3. The medium of claim 1, wherein the solution further contains 3-(N-morpholino) propanesulfonic acid (MOPS).

4. A medium for extracellular vesicle production, the medium comprising:
at least one peptide, where the peptide is selected from the group consisting of: peptides comprising an amino acid sequence of SEQ ID NO: 16 to SEQ ID NO: 21; and a solution containing a sugar.

5. The medium of claim 4, wherein the sugar is at least one selected from the group consisting of glucose, sucrose, and sorbitol.

\* \* \* \* \*